United States Patent [19]
Shofner et al.

[11] Patent Number: 5,539,515
[45] Date of Patent: Jul. 23, 1996

[54] APPARATUS AND METHODS FOR MEASUREMENT AND CLASSIFICATION OF TRASH IN FIBER SAMPLES

[75] Inventors: Frederick M. Shofner; Michael E. Galyon; Joseph C. Baldwin; Youe-T Chu, all of Knoxville, Tenn.

[73] Assignee: Zellweger Uster, Inc., Knoxville, Tenn.

[21] Appl. No.: 333,530

[22] Filed: Nov. 2, 1994

Related U.S. Application Data

[63] Continuation of Ser. No. 2,712, Jan. 11, 1993, abandoned, which is a continuation-in-part of Ser. No. 962,898, Oct. 16, 1992, Pat. No. 5,469,253, and Ser. No. 493,961, Mar. 14, 1990, Pat. No. 5,270,787.

[51] Int. Cl.⁶ .......................... G01N 21/89; G01N 15/14; G01L 5/04
[52] U.S. Cl. .......................... 356/238; 73/160; 356/383; 356/385
[58] Field of Search .......................... 356/238, 383–387, 356/43, 430; 19/23, 25, 300, 200; 250/560, 559.01; 73/160

[56] References Cited

U.S. PATENT DOCUMENTS

| | | |
|---|---|---|
| 3,069,964 | 12/1962 | Simon . |
| 3,816,001 | 6/1974 | Duncan et al. . |
| 3,936,665 | 2/1976 | Donoghue . |
| 4,027,162 | 5/1977 | Knollenberg . |
| 4,511,253 | 4/1985 | Glockner et al. .......................... 356/385 |
| 4,512,060 | 4/1985 | Shofner .......................... 19/200 |
| 4,631,781 | 12/1986 | Shofner .......................... 19/200 |
| 4,634,280 | 1/1987 | Paulson, Jr. .......................... 356/385 |
| 4,686,744 | 8/1987 | Shofner .......................... 19/200 |
| 4,764,876 | 1/1990 | Whitener, Jr. et al. .......................... 73/160 X |
| 4,885,473 | 12/1989 | Shofner et al. .......................... 250/574 |
| 4,891,974 | 1/1990 | Wassenhoven .......................... 73/160 |
| 5,130,559 | 7/1992 | Leifeld et al. .......................... 250/562 |
| 5,270,787 | 12/1993 | Shofner et al. . |
| 5,383,135 | 11/1995 | Shofner et al. .......................... 364/552 |

FOREIGN PATENT DOCUMENTS

| | | |
|---|---|---|
| 0226070 | 3/1958 | Australia . |
| 225009 | 10/1987 | European Pat. Off. . |
| 2408117 | 6/1979 | France . |
| 02111624 | 12/1983 | Japan . |
| 2031960 | 4/1980 | United Kingdom . |
| WO89/01619 | 7/1988 | WIPO . |

OTHER PUBLICATIONS

Shofner, Frederick M., et al., "Advance Fiber Information System: A New Technology for Evaluating Cotton," (Dec. 1988).

Lord, E. And Heap, S. A., "The Origin and Assessment of Cotton Fibre Maturity," International Institute for Cotton (Dec. 1988) pp. 1–38.

Thibodeaus, Devron, P., et al., "An Absolute Reference Method for Determination of the Maturity of Cotton Fibers," (1988).

(List continued on next page.)

*Primary Examiner*—Vincent P. McGraw
*Assistant Examiner*—K. P. Hantis
*Attorney, Agent, or Firm*—Luedeka, Neely & Graham; Andrew S. Neely

[57] ABSTRACT

An apparatus and method for measuring characteristics of entities in a sample of textile material, including trash, provides a sample of textile material to a processor where entities are individualized and thereafter transported to a sensor system. Characteristic signals are generated by the sensor signal corresponding to sensed characteristics of the entities, including trash, and a computer analyzes the characteristic signals to identify signals corresponding to trash and to classify the trash signals as corresponding to one of several types of trash. Based on the characteristic signals, the computer determines an entity length, diameter and speed and also determines a peak value of a characteristic signal corresponding to an entity. Based on these measurements, trash is characterized as to one of several types of trash.

1 Claim, 22 Drawing Sheets

OTHER PUBLICATIONS

Bragg, C. K. (1990) "A Rapid Measurement of Short Fiber Content" 20th International Conference, Bremen.

Faserforshung und Textiltechnik 25 (1974) Heft–12 Zeitschrift fur Polymerforschung (pp. 528–536).

Frey, M. (1990) "Practical Experience with New Cotton Measuring Methods" 20th International Cotton Conference, Bremen, Germany. Faserinstitut Breman e.V.

Thibodeaux, D. P. (1990) "Update of Special Applications of Cotton Maturity Testing" 20th International Cotton Conference, Bremen, Germany. Faserinstitut Bremen e.V.

Deussen, H. et al. (1988) "Why does the Need for Finer, Stronger, and Cleaner Cotton Fibers Require a Change in the Cotton Grading and Marketing System/" W. Shlafhorst & Co. Doc No. 21 Monchengladback, Germany.

Shofner, Frederick M., et al., "An Overview of the Advanced Fiber Information System," (Mar. 1990).

(Catalogue pages) "Performance, Accuracy, Effciency: Spinlab HVI 900 System" no date.

"Fiber Testing USTER® AFIS–T Measuring Trash and Dust Particles in Cleaning and Carding" 4 pages (Sep. 1991).

"Trash Testing–MDTA 3 and AFIS–T" (prepared for ITMA 1991, Hanover).

Shofner et al, "Advanced Fiber . . . Cotton", Dec. 1988.

(SECTION 3-3)

| SIDE VIEW | END VIEW | |
|---|---|---|
|  |  | BARK |

| | | |
|---|---|---|
|  |  | LEAF OR GRASS |

| | | |
|---|---|---|
|  |  | SEED COAT FRAGMENT |

| | | |
|---|---|---|
|  |  | DUST |

| | | |
|---|---|---|
|  |  | FIBER FRAGMENT |

APPARATUS AND METHODS FOR MEASUREMENT AND CLASSIFICATION OF TRASH IN FIBER SAMPLES

CROSS REFERENCE TO RELATED APPLICATIONS

This application is a continuation of application Ser. No. 08/002,712 now abandoned, filed on Jan. 11, 1993, which was a continuation-in-part of application Ser. No. 07/962,898 filed on Oct. 16, 1992 now U.S. Pat. No. 5,469,253 entitled, "Apparatus and Method for Testing Multiple Characteristics of Single Textile Sample With Automatic Feed" and application Ser. No. 07/493,961, filed Mar. 14, 1990, now U.S. Pat. No. 5,270,787 entitled "Electro-Optical Methods and Apparatus for High Speed Multivariate Measurement of Individual Entities in Fiber or Other Samples" whose disclosure is incorporated herein by reference.

FIELD OF INVENTION

The present invention relates to apparatus and methods for monitoring properties of fiber samples and particularly relates to an apparatus and method that classifies trash in fiber samples into one of several classes of trash, such as fibrous or other, bark or grass, etc.

BACKGROUND OF INVENTION

The predecessor instrument to the present invention is manufactured by Zellweger Uster, Inc. and is known as AFIS. This instrument separated fibers and neps into one airstream and trash into another airstream using the device disclosed in U.S. Pat. No. 4,512,060. Trash is defined as foreign matter having size greater than about 50 μm. Sometimes this foreign matter is called dust and trash but we shall use the designation trash here for simplicity. In this predecessor, AFIS, it was necessary to test three sets of replicate samples of textile material separately to determine information about fibers, neps and trash. One test and one separate sample of textile material was necessary for each type of entity for each replicate. Although this AFIS provided the best data available at the time for automated and fast textile testing instruments, there was a need for better data and increased speed. An improved sensor was discovered and is disclosed in the co-pending application Ser. No. 07/493,961, and the instrument incorporating the improved sensor, also known as AFIS, is manufactured by Zellweger Uster, Inc. For clarity and consistency with the references, the first instrument is called AFIS-0 and the instrument with the improved sensor is called AFIS-1.

The present invention is a further improvement in AFIS-1 and is directed primarily to testing rate considerations. It was first discovered that the improved sensor of AFIS-1 produced data that would enable substantially simultaneous measurement of multiple data from the same sample of textile material. By substantially simultaneous it is meant that nep data, fiber data and trash data are obtained by testing a single sample of textile material and detecting and measuring substantially all of the neps and trash and detecting and measuring a representative sample of the fibers. Thus, this improvement eliminates the need to run three separate tests on typically 3–5 replicates of three separate samples to obtain data for neps, trash and fiber. Also, it was discovered that such data could be obtained using only one sensor, if desired. The testing speed improvements discussed above are made possible by a new analyzer circuit, which is a hybrid analog and digital circuit in the preferred embodiment. Speed of operation is increased by a factor of three in the present invention as compared to AFIS-1 or AFIS-0.

With the advent of high speed handling, the need for accurate and high speed characterization of entities in a test sample is necessary. Although the basic count and size information of trash and individual fibers is sometimes sufficient, more detailed information about neps and trash is required.

Neps in staple textiles are broadly defined to be small clumps or entanglements of fiber. They are one of the three main constituents of staple fiber. However, neps may be broken down into three further categories; mechanically generated neps, seed coat neps, and shiny (or immature) neps. A mechanically generated nep is created during the opening, ginning, and carding of the cotton and can range from 0.1 mm to 5 mm in diameter. They are tightly knotted cotton or man-made fibers consisting of a tangled core and a long fiber tail that cannot be opened during processing. Seed coat neps or seed coat fragments are composed of a collection of fibers that remain attached to the shell of the cotton seed. When viewed in visible light, they are small tufts of fibers attached to a dark central core. A shiny nep or dye resistant nep is a collection of very immature or dead cotton fibers. These are formed on the cotton seed when a part or all of the cotton seed undergoes stress that stops the maturation process of the fibers. The resulting fibers are very thin and weak with very little lateral stiffness and can easily form tight clumps of closely packed, parallel fibers. These very immature fibers cannot absorb dyestuffs properly and result in white specks and discolorations in finished fabric. These shiny neps may or may not be attached to the seed coat.

With these descriptions in mind, it is easy to understand the importance of classifying neps into these categories. Mechanically generated neps are indicative of the aggressiveness of the processing machinery and, therefore, an accurate count of these particles is used to fine tune or even overhaul processing machinery. The distinction between polyester, the most common man-made fiber, and cotton neps is important as they are often processed separately and combined in sliver form at a drawing frame.

Seed coat fragments originate from the cotton plant and their numbers are influenced by the method of ginning and cleaning and the species of cotton. Seed coat fragments are particularly troublesome in that they are a major source of yarn defects. The number of these particles per unit weight provide useful information to the grower about seed-to-fiber tenacity, to the ginner about the aggressiveness of the seed removal process and to the processor about the quality of the raw material.

Shiny nep counts predict the dyeability of the processed and spun cotton. Specifically, the number of these shiny neps per gram predicts the quality of the appearance of the finished and dyed fabric allowing the quality conscious mill operator to direct the highest quality material to the most demanding applications.

The quantity and quality of trash in a sample of fiber is important to textile processors for reasons analogous to those discussed above. Trash occurs in cotton primarily as a result of mechanical picking and such trash may be classified as fibrous or non-fibrous and may be further subclassified as fibrous bark, fibrous grass or leaf, flake grass or leaf, thick trash (seed coat fragments and some bark), dust or fiber fragments. The classification of trash in a sample will reveal problems in prior processing, will facilitate corrective processing, and will help predict the quality of the end product (usually yarn) produced from the fiber.

Therefore, before any textile processor can significantly increase the efficiency or quality of their processing, much more detailed information about the raw materials, and particularly neps, is required. This need extends from the cotton grower and ginner up through the yarn or thread spinner and finally to the fabric mill.

SUMMARY OF INVENTION

In accordance with the present invention, an apparatus is provided for measuring characteristics of entities in a sample of textile material where the sample includes at least trash. The sample of textile material is provided from a supply and a processor receives the textile sample and processes it to release the entities of the sample one from the others, individualizes the entities and produces the sample at an output. A transport is provided for transporting individualized ones of the entity to a sensor system where at least one characteristic of a portion of the entities, including trash, being moved by the transport are sensed. The sensor system produces characteristic signals corresponding to the sensed characteristics, and these signals are provided to a computer where they are analyzed. The computer identifies signals that correspond to trash and further analyzes the trash signals to classify the signals as corresponding to one of several types of trash.

In a particular apparatus and method of the present invention, the length of the entity is determined based on the characteristic signals and the length is compared to a threshold. Based in part on this comparison, the trash is classified as to one of several types of trash.

In accordance with another aspect of the present invention, a diameter is determined that corresponds to a diameter characteristic of the entity sensed by the sensor system. It will be understood that the term "diameter" is being used in a very broad sense in this application because trash is highly irregular and would not have a precise geometric diameter. In this application, the diameter may also be thought of as a width when the entity is viewed in a two-dimensional profile. After the diameter is determined, a ratio based upon the length as compared to the diameter is compared to a threshold. Preferably, the length is divided by the diameter to determine an aspect ratio and that aspect ratio is compared to a threshold of 3. Again, based on the comparison of the ratio to the threshold, the trash is classified.

In accordance with another aspect of the present invention, speed of an entity is sensed by the sensor and determined by analyzing the characteristic signals. The speed is compared to a threshold and the entity is classified based in part upon the comparison of the speed to the threshold. The term "speed" is also used broadly in the present invention, and it may be thought of as a number representing the speed of the entity. However, it is not necessary that "speed" be a number that is expressed in units of distance divided by time. For example, the present invention determines speed by measuring the time required for an entity to pass from a first point to a second point. That measure of time is, in fact, a measure of speed and it will be understood that the term "speed" as used herein should incorporate time measurement as well.

In accordance with another aspect of the present invention, a peak value is determined for a characteristic signal corresponding to trash. This peak value is compared to a threshold and the entities are classified as to one of several types of trash based in part on the comparison of the peak value to the threshold.

BRIEF DESCRIPTION OF THE DRAWINGS

The present invention may best be understood by reference to the following Detailed Description of preferred embodiments when considered in conjunction with the Drawings in which.

DETAILED DESCRIPTION

Figure 1:
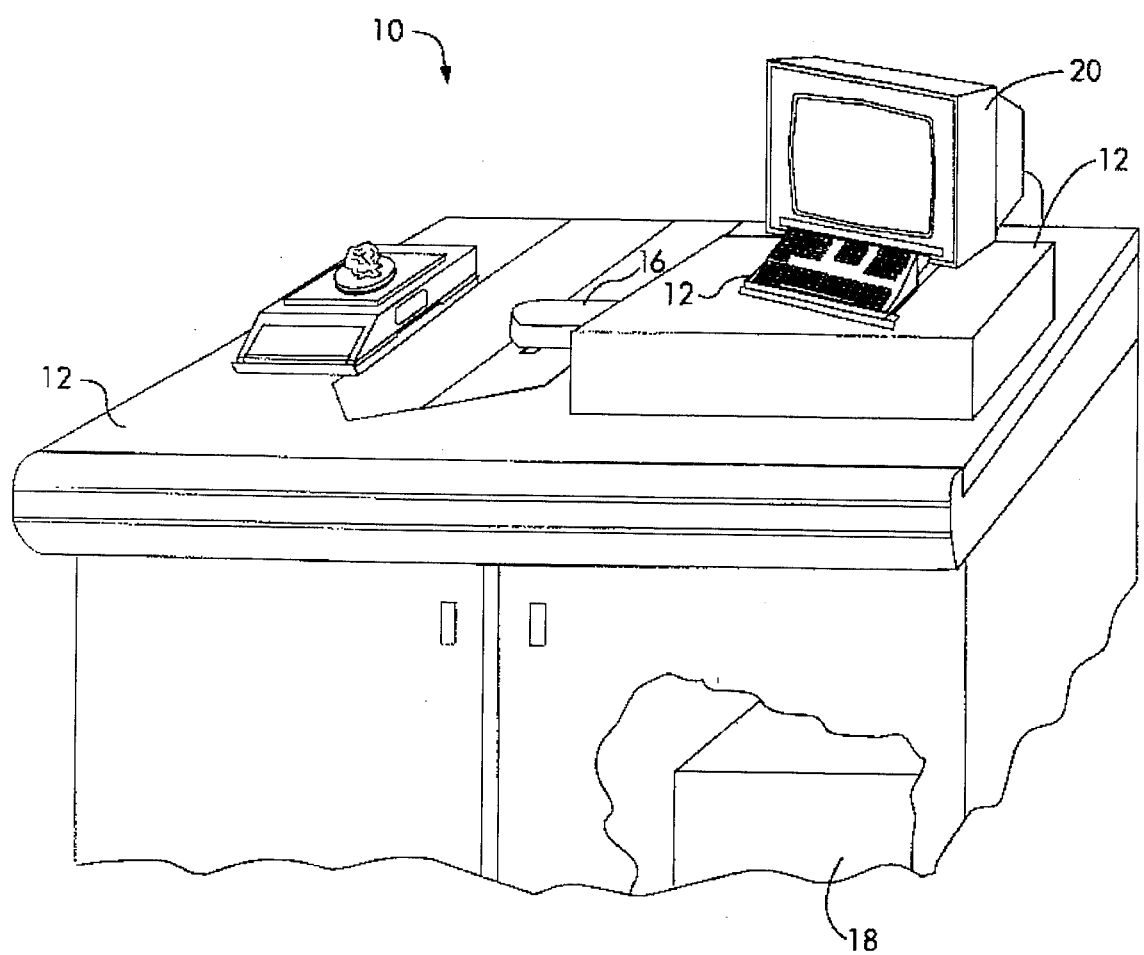
FIG. 1 is a perspective view of the exterior of a fiber testing apparatus, a preferred embodiment of the present invention.

Referring now to the drawings in which like reference characters designate like or corresponding parts throughout the several views, there is shown in FIG. 1 an external view of the textile testing apparatus 10 constituting a preferred embodiment of the present invention. The testing apparatus 10 includes a main housing 12 with an automatic carousel 14 mounted on the top of housing 12 for holding textile material samples. A feed head 16 extends from the carousel 14 for loading textile samples into the testing apparatus 10.

The operation of the testing apparatus 10 is under control of a computer 18 which interfaces with the operator through a display 20 and a keyboard 22. In the preferred embodiment, the testing apparatus 10 is used to test textile materials and is particularly designed to measure the characteristics of textile fibers, neps and trash, but the testing apparatus 10 would be equally operable on any entity having size and weight characteristics that are comparable to the aforementioned textile entities.

Figure 2:
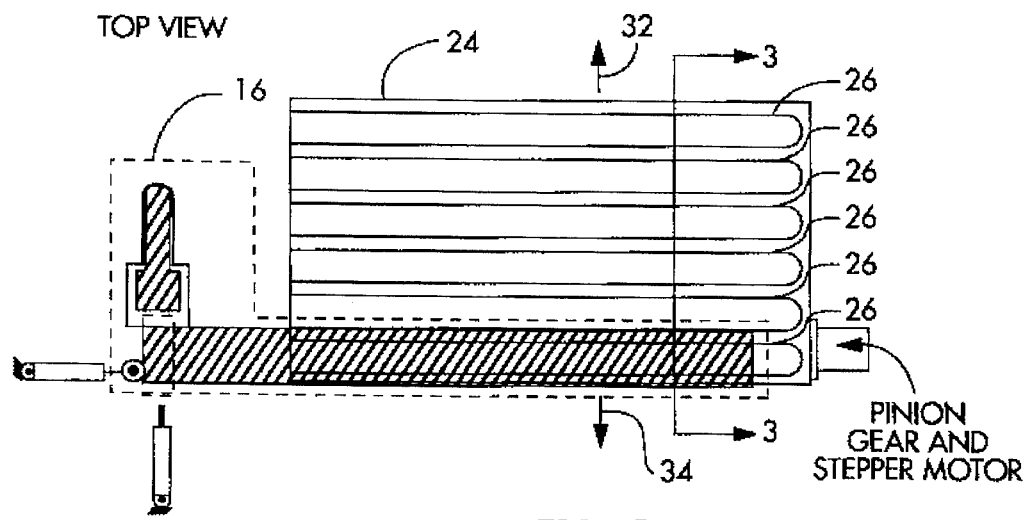
FIG. 2 is a somewhat diagrammatical cross-sectional view of an automatic feed mechanism including a magazine.
Figure 3:
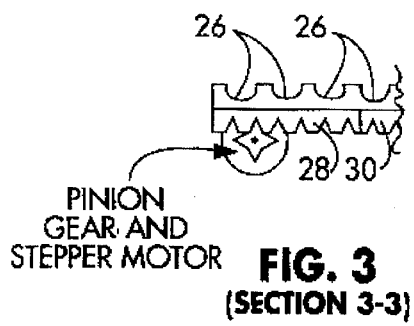
FIG. 3 is a somewhat diagrammatical cross-sectional end view of the magazine shown in FIG. 2.

Referring now to FIG. 2, a somewhat diagrammatic top view of a magazine 24 and feed head 16 is shown. The magazine 24 is contained within the carousel 14 shown in FIG. 1, and it includes a plurality (20 to 200) of receptacles 26 that extend the length of the magazine 24 and accept elongate samples of textile materials. In FIG. 3, a cross-sectional diagrammatic view of a portion of the magazine 24 is shown. As best shown in FIG. 3, the receptacles 26 are channels formed in the magazine 24 to a depth of approximately one inch and having a horizontal width of approximately one inch. The magazine 24 is carried on a rack 28 that is driven by a stepper motor 30 to move the rack horizontally in the directions indicated by arrows 32 and 34 in FIG. 2. Thus, the stepper motor 30 selectively moves magazine 24 (or indexes the magazine 24) horizontally to align a desired receptacle 26 with the feed head 16. Once the desired channel 26 is in proper registry with the feed head 16, the sample within that particular receptacle 26 is removed by the feed head 16 and delivered to the testing apparatus 10 for testing.

Figure 4:
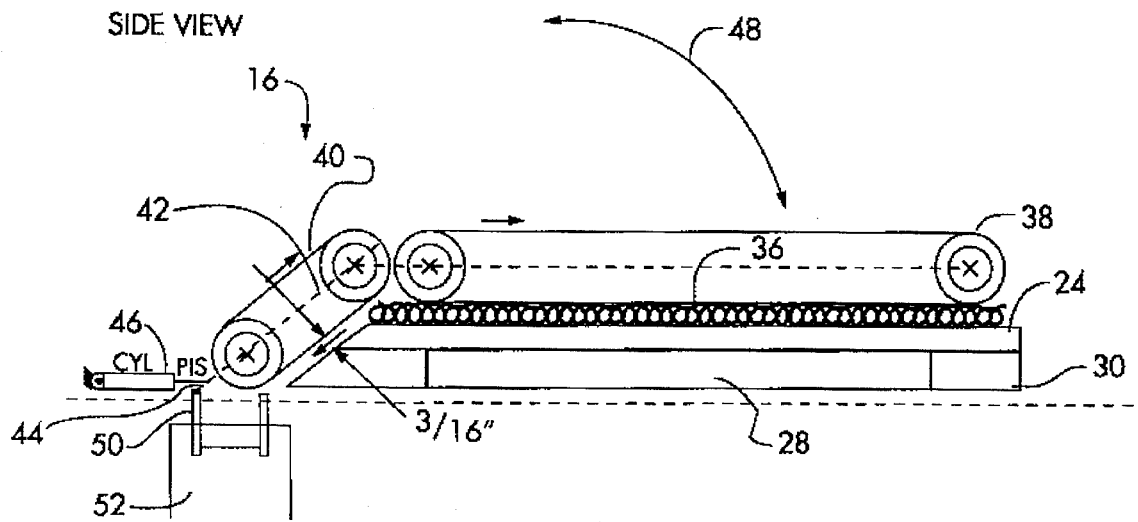
FIG. 4 is a somewhat diagrammatic cross-sectional view of the feed head and magazine.

Referring now to FIG. 4, a diagrammatic side cross-sectional view of the feed head 16 and the magazine 24 is shown. As shown in FIG. 4, an elongate slender textile sample 36 is positioned on the magazine 24 in one of the receptacles 26. The sample 36 is engaged by feed head belts 38 and 40 which are mounted on a frame represented by dashed line 42. The frame 42 is pivotally mounted on a pivot pin 44 and the position of the frame 42 is controlled by a piston and cylinder set 46 which raises and lowers the frame 42 along the arc indicated by arrow 48. Thus, the piston and cylinder set 46 is operable to lower the belts 38 and 40 into engagement with the sample 36 and raise the belts 38 and 40 away from the sample 36 and magazine 24 so that the magazine 24 may be moved without interference from the belts 38 and 40. The belts 38 and 40, when they engage the sample 36, drive the sample 36 into a top feed roll 50 which, in turn, delivers the sample to a feed tray 52.

Figure 5:
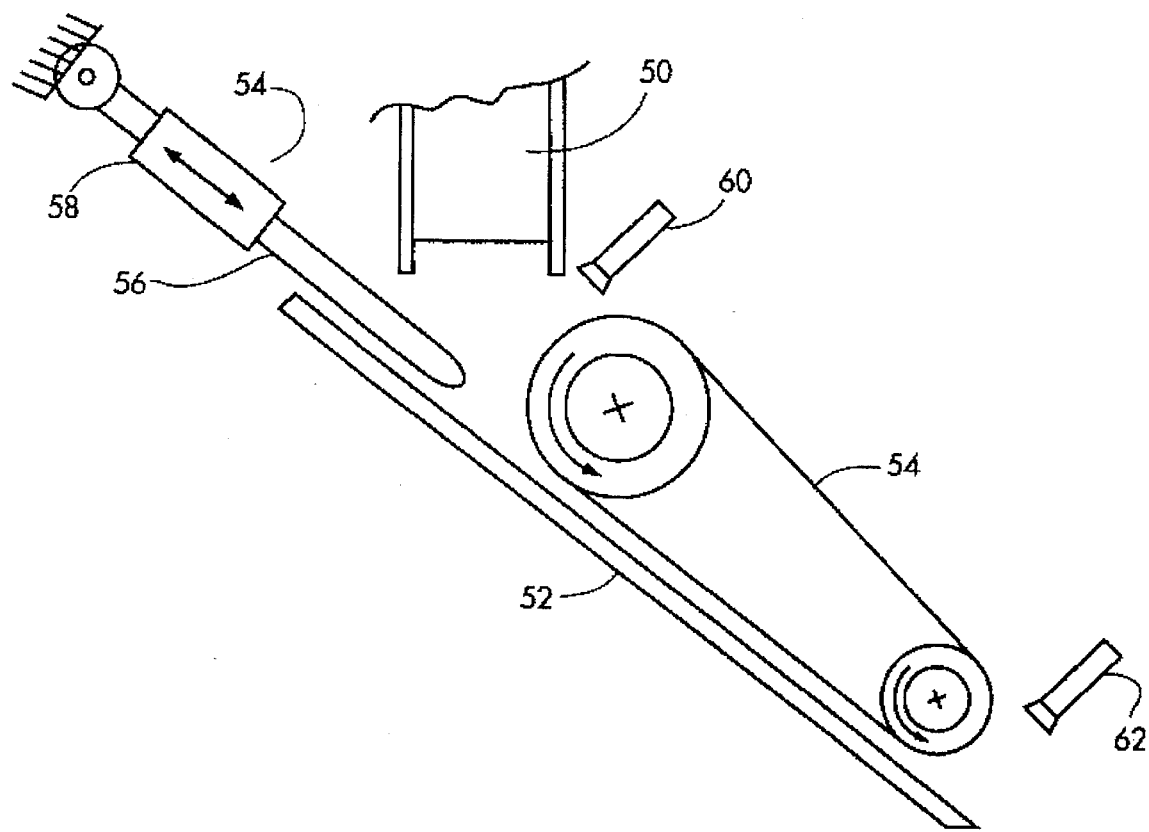
FIG. 5 is a somewhat diagrammatical side cross-sectional view of a feed finger and feed rollers.

Referring now to FIG. 5, a side view of the tray 52 is shown. The top feed roller 50 delivers the sample to the feed tray 52 and a plunger 54 engages and drives the sample under a tray feed belt 54 which is mounted immediately above and parallel to the feed tray 52. The tray feed belt 55 drives the sample down the feed tray 52 and is the last step performed in the automatic feed head 16 of the testing apparatus 10. Optical sensors 60 and 62 are provided for detecting the presence or absence of a sample 36 of textile material in the feed mechanism 16. Sensor 60 is positioned at the output end of the feed belt 50 viewing the feed tray 52 in the area of the feed tray that is traversed by the plunger finger 56. Optical sensor 62 is positioned at the end of the tray feed belt 55 viewing the feed tray 52.

In FIGS. 2, 3, 4, and 5 it will be understood that the illustrations of feed belts 38, 40, 50, and 55 represent the drive mechanisms, including motors, controls, and interconnections therefor, that are necessary to operate a feed belt in a conventional manner. Likewise, the representations of optical sensors 60 and 62 represent conventional sensors with conventional power supplies and control interconnections. Again, the piston and cylinder set 46 and the plunger 54 comprised of a dual action piston and cylinder set 58 and plunger finger 56 represent conventional piston and cylinder sets, including compressed air supplies and control mechanisms.

Figure 6:
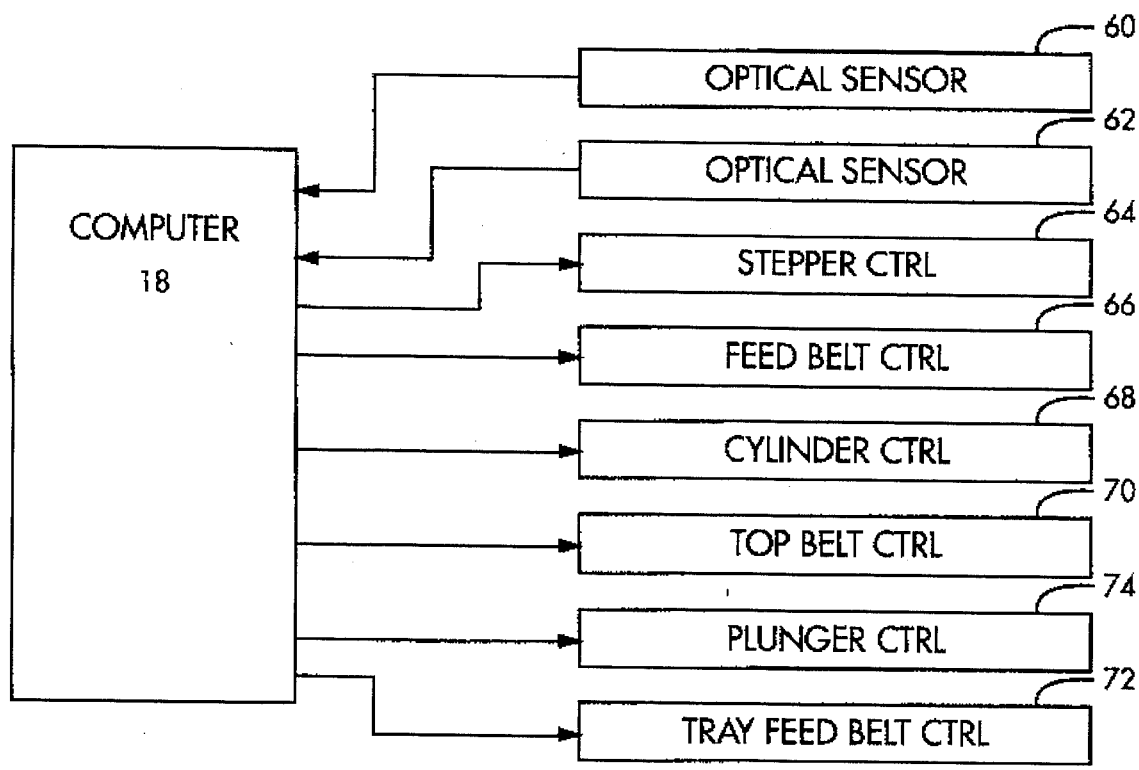
FIG. 6 is a block diagram of the computer and control system for operating the automatic feed mechanism.

The operation of these elements including their control elements may best be understood by reference to FIG. 6, a block diagram illustrating the computer 18 and control mechanisms used in the automatic feed head 16. Referring to FIGS. 2–6, when the testing apparatus 10 is turned on, the computer 18 issues a command to the stepper control 64 to drive the magazine 24 to its initial position aligning the first receptacle 26 with the automatic feed mechanism 16. When the magazine 24 is in the desired position, the computer 18 issues commands to the feed head belt control 66 and the cylinder control 68 which turns on the feed belts 38 and 40 and actuates the cylinder 46 to lower the belt 38 into engagement with the sample 36. The computer 18 also issues a start command to the top belt control 70 and the tray feed belt control 72 and thereby starts the operation of the top feed belt 50 and the tray feed belt 55.

After the computer 18 initiates commands that will cause the feed belts 38, 40 and 50 to deliver a sample to the feed tray 52, the computer 18 will monitor the signal from sensor 60 and, when a sample is detected on the tray 52, the computer 18 will issue commands to the plunger control 74 actuating the cylinder 58 of the plunger 54 to move the plunger finger 56 forward toward the tray feed roller 55 and drive the sample 36 on the tray 52 under the feed belt 54. If the computer 18 does not detect the presence of a sample at the sensor 62 within about one and one-half seconds after the plunger finger 16 has been actuated, the computer will issue another command to the plunger control 74 to actuate and cause the plunger finger 56 to force the sample under the tray feed roll 55. This process will be repeated five times and, if the sensor 62 does not sense the sample after the fifth repetition, the computer 18 will issue commands to stop all action of the feed mechanism 16 and display a fault condition on display 20 suggesting a sample jam in the feed mechanism.

Assuming there has been no jam, the computer 18 then analyzes the signals from the optical sensors 60 and 62 to determine whether a sample is present in the automatic feed mechanism 16. Under normal conditions, both sensors will indicate a presence of a sample 36. If neither sensor detects a sample, the computer 18 will wait another 10 seconds and analyze the signals from the optical sensors 60 and 62 again. If no sample 36 is detected by either sensor, the computer 18 will issue a command to the control cylinder 68 to raise the frame 42 and the feed belts 38 and 40 away from the magazine 24. Then, the computer 18 will issue a command to the stepper control 64 causing the stepper motor 30 to index the magazine 24 to align the second receptacle 26 with the feed mechanism 16. The computer 18 will then, again, issue commands to the cylinder control 68 to lower the feed belts 38 and 40 into engagement with a sample in the second receptacle 26. Again, the computer 18 will analyze the signals from the optical sensor 60 and 62 to determine the presence or absence of a sample and will continue indexing the magazine 24 forward until a sample is detected in the feed mechanism 16.

Assuming both optical sensors 60 and 62 initially sense the presence of a sample 36 in the feed mechanism 16, eventually the sample will be fed completely through the feed mechanism. The computer 18 periodically polls the signals from the optical sensors 60 and 62 and, when these sensors 60 and 62 indicate the absence of a sample 36 in the feed mechanism 16, it will wait for a predetermined dwell period, approximately ten seconds, and will check other operations of the testing apparatus 10. Assuming everything is functioning normally, after the dwell period the computer 18 will issue commands to the cylinder control 68 and the stepper control 64 to cause the magazine 24 to be indexed forward to the next receptacle 26.

When the sample from the last receptacle 26 has been loaded by the feed mechanism 16, or an attempt to do so has been made, the computer 18 assumes that the magazine 24 is now empty and it will display a prompt on the display 20 requesting the operator to reload the magazine 24 with textile samples and re-initiate the automatic feed process.

Figure 7:
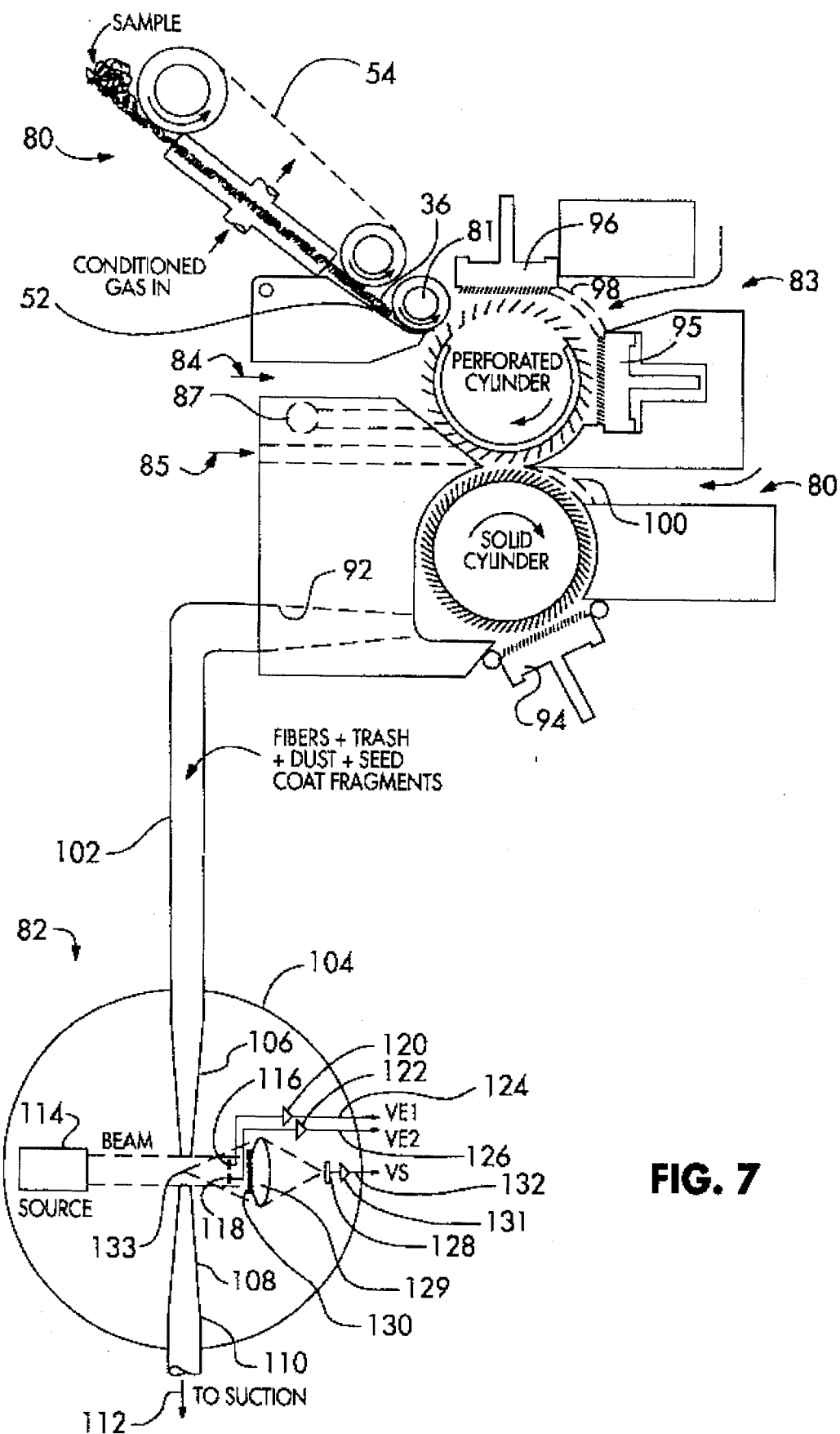
FIG. 7 shows an embodiment of an entity individualizer that receives samples from the automatic feed mechanism and a single sensor that receives entities from the individualizer.

Referring now to FIG. 7, there is shown a fiber individualizer 80 and a sensor 82. The individualizer 80 receives textile samples 36 from the feed tray 52 and feed tray belt 55. The function of the individualizer 80 is to release and individualize entities that are fed to it. In the preferred embodiment, the individualizer 80 releases neps, trash and fibers one from the others and individualizes the various types of entities.

The individualizer 80 includes a feed roller 81 that receives the sample on the feed tray 52 and feeds the sample 36 into the individualizer 80. Conditioned air is input into the individualizer through air supply channels 83, 84, 85 and 86. (Compressed air which purges or cleans the individualizer is supplied for brief periods, such as 0.5 seconds, via channel 87.) The sample 36 is fed in a controlled manner to the individualizer 80 by the feed roller 81 and the entities are processed by the perforated cylinder 88 and the solid cylinder 90 in combination with the carding flats 94, 95 and 96. This processing releases the entities, such as neps, fibers, and trash, one from the others, and individualizes the entities so that the entities are delivered one at a time (in an individualized condition) at the output 92 of the individualizer 80.

The individualizer 80 is substantially the same as that disclosed in U.S. Pat. No. 4,512,060 and that disclosure is incorporated by reference. The major difference in construction of the individualizer 80, as compared to U.S. Pat. No. 4,512,060, is the provision of staggered double baffles 98 and 100 that are provided across air supply channels 83 and 86. The baffles 98 and 100 allow air to flow into the individualizer through the baffles plates 98 and 100, but the plates 98 and 100 prevent trash or other particles from being thrown out of the individualizer through the air passages 83 and 86. Thus, in contrast to the individualizer shown in U.S. Pat. No. 4,512,060, all of the entities that are processed by the individualizer 80 are output through the individualizer output 92 and into a conduit 102. The conduit 102 carries the entities in an airstream into a sealed chamber 104. The end of the conduit 102 terminates in a nozzle 106 and an opposing nozzle 108 is positioned in the chamber 104 in substantial alignment with the nozzle 106 such that an opening is formed between the two nozzles 106 and 108. The nozzle 108 is connected to conduit 110 which, in turn is connected to a vacuum source 112 that provides the vacuum and creates the airstream in the conduits 102 and 110 and the nozzles 106 and 108. A source of light 114 is provided in the chamber 104 and directs light through the opening between the nozzles 106 and 108 toward two extinction detectors 116 and 118 that are positioned side by side as shown in FIG. 7. With respect to the airstream in the nozzles 106 and 108, detector 118 is positioned downstream from the detector 116. The outputs of the detectors 116 and 118, are fed through amplifiers 120 and 122, respectively, and output extinction signals VE1 and VE2 are produced on lines 124 and 126.

A forward scatter detector 128 including a lens system 129 and a light stop 130 is provided for detecting light that is scattered forward at an angle of about 40° (in the preferred embodiment) by entities 133 passing through the opening between nozzles 106 and 108. The output of the forward scatter detector 128 is applied through an amplifier 131 to produce a forward scatter signal, VS on line 132.

The sensor 82 as described above is substantially identical to the sensor described in co-pending application Ser. No. 07/493,961 whose description is incorporated herein by reference.

Figure 8:
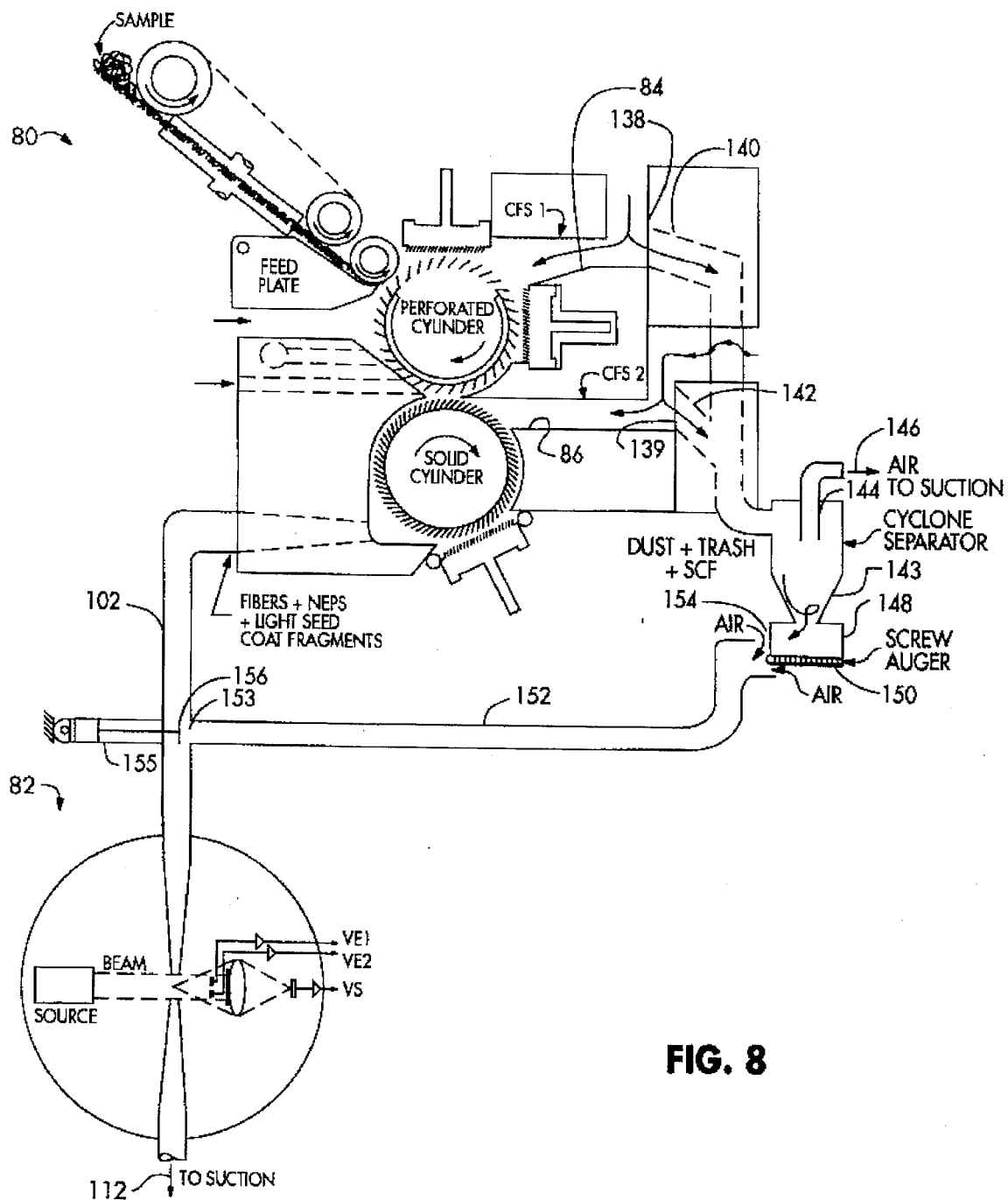
FIG. 8 is a somewhat diagrammatical view of an alternate embodiment of the individualizer and sensor system.

FIG. 8 represents an alternate embodiment combining the individualizer 80 and sensor 82. In this embodiment, the sensor 82 is identical to that shown and described in FIG. 7 and the individualizer 80 is substantially identical to that described in U.S. Pat. No. 4,512,060, except in the manner in which trash is handled after it leaves the individualizer 80. In the embodiment of FIG. 8, the baffles 98 and 100 are not used and trash is ejected through the air channels 84 and 86, counterflow slots, CFS. The cylinders 88 and 90 propel the trash particles through the passageways 84 and 86 in opposition to the airflow therein. When the trash particles reach the air intakes 138 and 139 their momentum carries them into the conduits 140 and 142 and they are transported in an airstream flowing away from the individualizer 80. The conduits 140 and 142 are input to a cyclone separator 143 that includes a vertical conduit 144 extending upwardly to an air suction 146. The suction 146 provides the suction needed to form the airstream in conduits 140 and 142. Air and very fine particles leave the separator 143 through the conduit 144 but most of the dust and trash particles are separated by outward centrifugal forces and settle by gravity into the chamber 148 and are selectively ejected from the chamber by an auger 150.

Upon command from the computer 18, the trash particles are augured out of the chamber 148 where they are picked up by an airstream in a conduit 152. An air intake 154 is provided adjacent to the auger output. The airstream in the conduit 152 carries the trash particles to an intake 153 in the conduit 102. A piston and cylinder set 155 selectively covers and uncovers the intake 153 with a cover plate 156 mounted on the piston and cylinder set 155. The piston and cylinder set and the auger 150 are under the control of the computer 18. When it is desired to measure the characteristics of fibers and neps, the cover plate 156 is moved against the intake 153 and fibers and neps are supplied to the sensor 112 substantially without trash content. Then, when it is desired to measure trash characteristics, the computer 18 actuates the piston and cylinder set 154 to uncover the intake 153 and the computer 18 actuates the auger 150 to begin ejecting dust and trash from the chamber 148. The suction 112 then creates an airstream in the conduit 152 that carries the trash particles through the conduit 152, into the conduit 102 and finally through the sensor 82.

Figure 9:
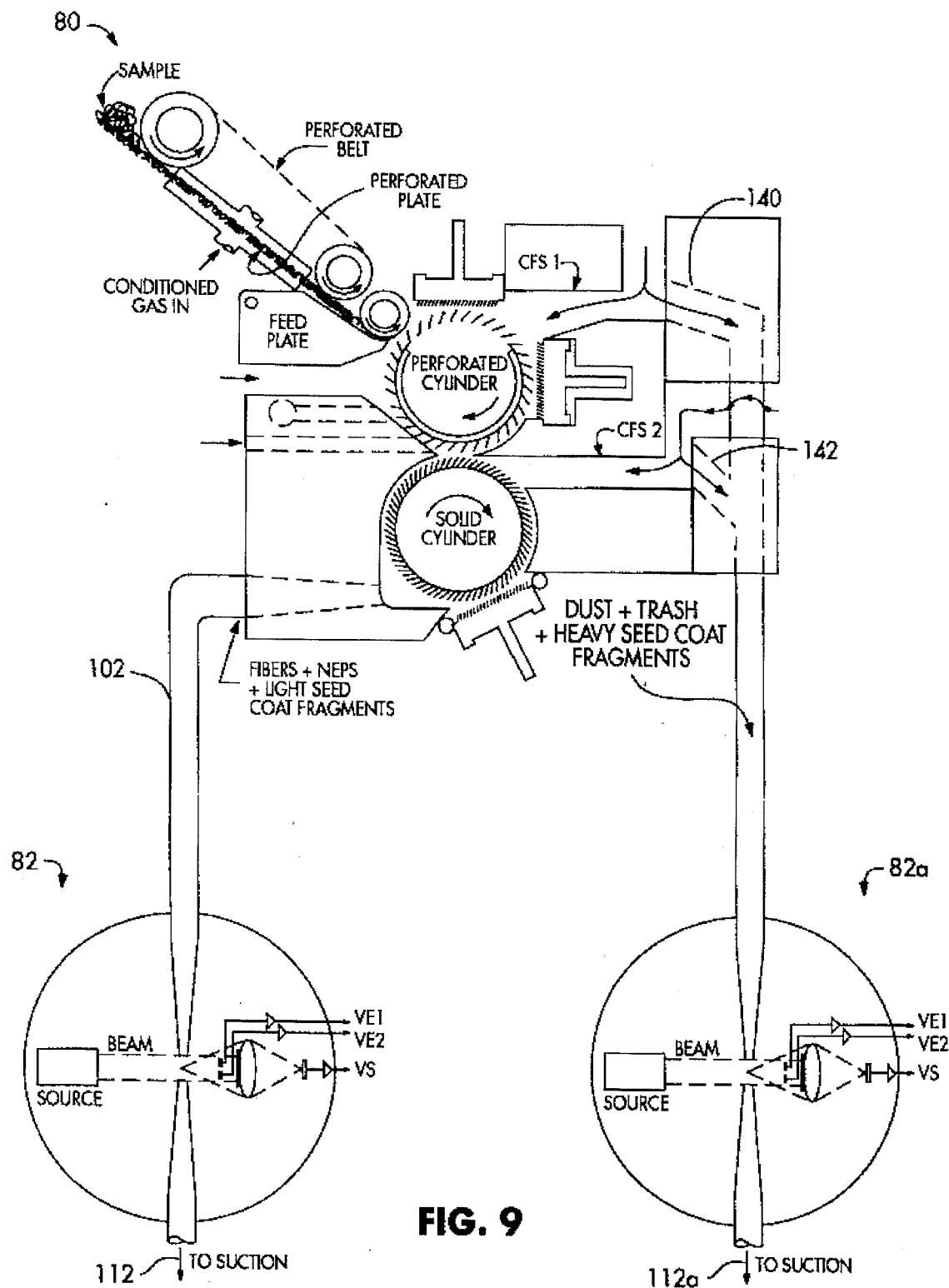
FIG. 9 is another embodiment of the individualizer and sensor system.

Yet another alternate embodiment is shown in FIG. 9. In this embodiment, the individualizer 80 is substantially the same as that shown in U.S. Pat. No. 4,512,060 except that the conduits 140 and 142 are combined into a single conduit 140 and connected to a separate sensor 82a. The airstream in conduit 141 is provided by a suction 112a that is approximately identical to the suction 112 of sensor 82. The application of the above three embodiments represented by FIGS. 7, 8 and 9 can be best understood in light of the operation of the sensor, the data acquisition boards, and the computer 18 which are described below.

Figure 10:
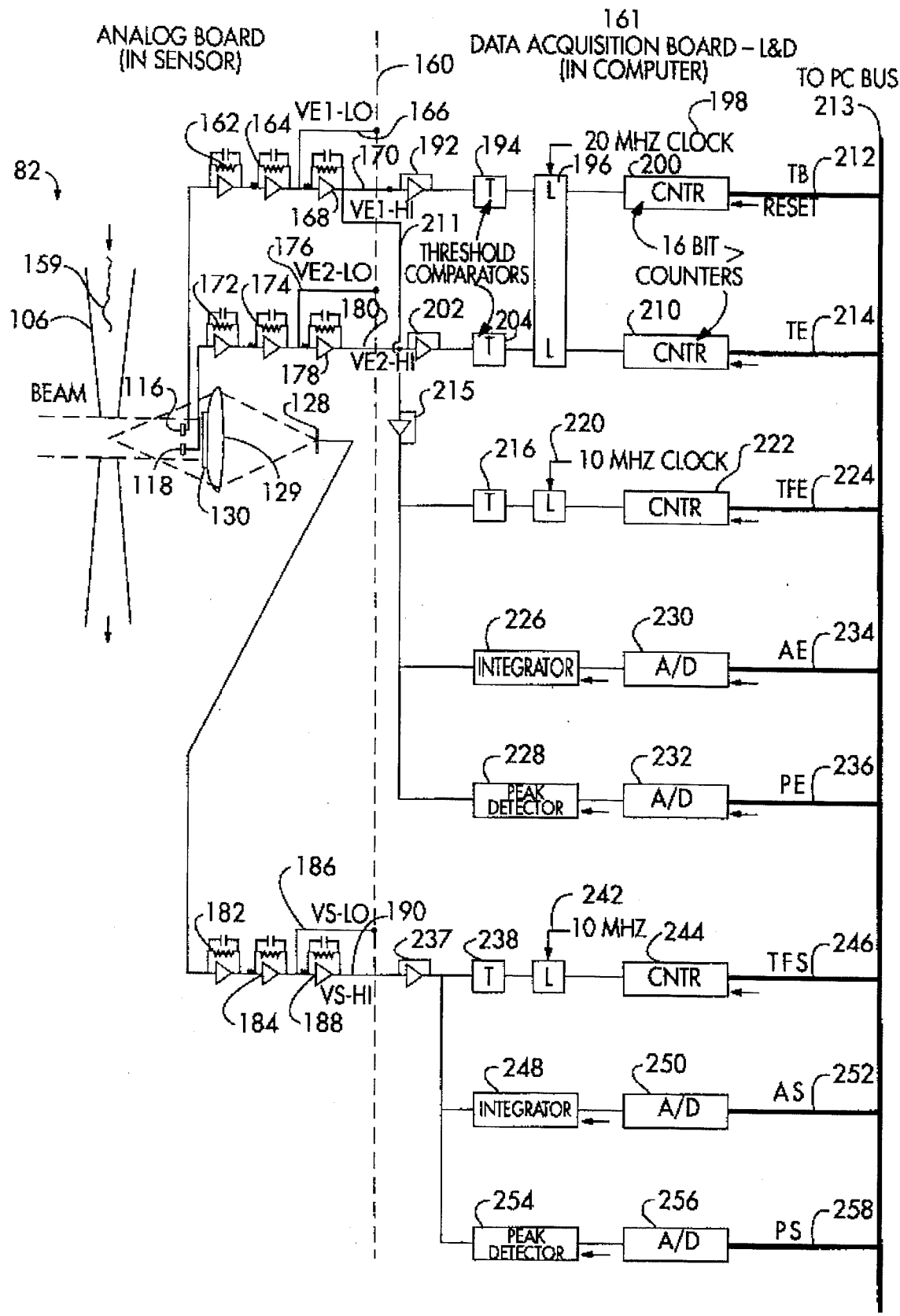
FIG. 10 is a block diagram of the analyzer system showing the detectors and analog amplifiers of the sensor and one data acquisition board.

In FIG. 10, a schematic diagram of the sensor 82 and one data acquisition board (DAB) 161, a dashed line 160 indicates the physical division between the sensor 82 and a data acquisition board (DAB) 161, shown here as a DAB responding to an individual fiber 159 moving in nozzle 106. Referring to the left hand side of FIG. 10, the sensor 82 is shown in greater detail. An extinction sensor 116 provides an output to an trans-impedance amplifier 162 whose output is amplified by an amplifier 164 having a voltage gain of approximately 4.3. The output of amplifier 164 appears on line 166 and constitutes the low gain channel of the first extinction sensor (VE1-LO). The output of amplifier 164 is applied through amplifier 168 having a gain of 12.5 and the output of amplifier 168 appearing on line 170 constitutes the high gain channel of the first extinction signal (VE1-HI).

In a similar construction, the output of the second extinction sensor 118 is applied through a transimpedance amplifier 172 to a voltage amplifier 174 having a gain of about 4.3. The output of amplifier 174 appears on line 176 and constitutes the low gain channel of the second extinction signal (VE2-LO). The output of amplifier 174 is also applied through an amplifier 178 having a gain of about 12.5 and the output of amplifier 178 appears on line 180 and constitutes the high gain channel of the second extinction signal (VE2-HI).

The forward scatter sensor 128 produces a signal that is provided to a trans-impedance amplifier 182 whose output is provided to an amplifier 184 having a voltage gain of about 20. The output of amplifier 184 appears on line 186 and constitutes the low gain channel of the scatter signal (VS-LO). The output of amplifier 184 is also applied through amplifier 188 having a gain of about 12.5 and the output of amplifier 188, appearing on line 190, constitutes the high gain channel of the scatter signal (VS-HI).

Referring now to the right hand side of FIG. 10, the data acquisition board (DAB) 161 may be described in detail. The data acquisition board (DAB) 161 shown in FIG. 10 is connected for measuring characteristics of textile fibers, as opposed to neps or trash. In this arrangement, the high gain channel of the first extinction signal appearing on line 170 is applied through an inverting isolation amplifier 192 having a gain of −1 and then to a threshold comparator 194. The threshold comparator 194 goes high or turns on when the signal appearing at its input exceeds a predetermined value, preferably one-half volt, and the comparator 194 goes low or turns off again when the signal drops below 0.5 volts.

The output of the comparator 194 is applied to a logic chip 196 that also receives a twenty megahertz clock signal 198. The logic chip 196 selectively applies the twenty megahertz clock signal to a counter 200.

In like manner the high gain channel of the second extinction signal (VE2-HI) from sensor 118 appearing on line 180 is applied through an inverting isolation amplifier 202, a threshold comparator 204, the logic chip 196 and a counter 210.

In this construction, the counts appearing in counter 200 are applied through lines 212 to a computer bus 213 via data bus directional drivers and are referred to as TB. Likewise, the counts appearing in counter 210 are applied to a computer bus 213 through lines 214 and are known as TE.

Logic chip 196 applies clock pulses to the counter 200 beginning when threshold comparator 194 goes high and ending when threshold comparator 204 goes high. Chip 196 applies clock pulses to counter 210 beginning when threshold comparator 194 goes low (after previously going high) and ending when comparator 204 goes low (after previously going high).

The high gain extinction signal is also applied through line 211 and an inverting isolation amplifier 215 to a threshold comparator 216 that controls a logic chip 218. A ten megahertz clock signal on line 220 is also supplied to the logic chip 218 and under the control of the threshold comparator 216, the logic chip 218 applies the ten megahertz clock signal to a counter 222. The count of counter 222 is applied through lines 224 to a computer bus 213 and is known as TFE.

The inverted high gain first extinction signal appearing at the output of amplifier 215 is also applied to an integrator 226 and a peak detector 228 whose outputs are applied to analog to digital (A/D) convertors 230 and 232, respectively. The output of A/D converter 230 appears on lines 234 and is applied to the bus 213 and, likewise, the output of A/D convertor 232 is applied on lines 236 to the bus 213. These data are known as area from the extinction signal AE and peak amplitude of the extinction signal PE, respectively.

The high gain channel of the forward scatter signal appearing on line 190 is applied through inverting isolation amplifier 237 to a threshold comparator 238, an integrator 248, and a peak detector 254. The output of the threshold comparator 238 is applied to a logic chip 240 that also receives a ten megahertz signal on line 242. The logic chip 240 applies clock signals to a counter 244 when the output of isolation amplifier 237 exceeds one-half volt and, when the signal falls below one-half volt, the logic chip 240 stops applying the clock signal to the counter 244. The output of the counter 244 is applied through lines 246 to the bus 213 and is known as TFS.

The outputs of the integrator 248 are applied through an A/D convertor 250 and lines 252 to the bus 213 and, likewise, the output of peak detector 254 is applied through an A/D convertor 256 and lines 258 to the bus 213. They are known as AS and PS, respectively.

From the description set forth above, it should be appreciated that TB appearing on line 212 represents the time required for the beginning of an entity, a fiber in this case, to pass from an optical projection of sensor 116 to an optical projection of sensor 118. Thus, TB corresponds to the speed of the leading edge of the entity. TE appearing on lines 214 represents the time required for the trailing end of an entity to pass from an optical projection of sensor 116 to sensor an optical projection of 118 and, thus, corresponds to the speed of the trailing end of the entity. TF appearing on lines 224 represents the time required for an entity to pass completely by an optical projection of extinction sensor 116. Thus, the TF corresponds to a dimension of the entity (such as the length of a fiber) and this dimension can be calculated based upon the speed of the entity. The signal appearing on line 234 represents the time integral of the light extinguished by the entity, or the area under the waveform, AE. The number appearing on line 236 represents the peak amount of light extinguished by the entity or to the peak amplitude PE. The count, TFS appearing on lines 246 represents the time required for the entity to pass by an optical projection of the scatter sensor 128 and corresponds to a dimension (such as length) of the entity as measured by the scatter sensor 128. The signal appearing on line 252 represents the time integral of light scattered by the entity as detected by sensor 128, AS, and the signal appearing on line 258 represents the peak amount of light scattered by the entity, PS.

The function of the DAB 161 is seen to convert the analog signals from the electro-optical (E-O) sensor 82 into digital signals impressed on the computer bus 213 and designated as TB 212, TE 214, TFE 224, etc. These signals thus define E-O parameters. The E-0 parameters, in turn, are used to provide entity information, fiber length and diameter in the case of FIG. 10. Co-pending application Ser. No. 07/493,961 which focuses on the AFIS-1 sensor, generally discloses how length, diameter, fineness, or maturity information for individual fiber entities is determined. That application also discloses how sensor 82 provides nep or trash entity signals. Co-pending application Ser. No. 07/762,905 further discloses how a sensor 82 enables trash measurements and in particular, how such measurements are interpreted.

It can thus be appreciated that the DAB 161 of FIG. 10 represents a major improvement in signal processing capability. Further, instruments based on earlier disclosures were unable to simultaneously provide multiple entity data—fiber, neps, trash, etc—from a single sample. The DAB 161 of FIG. 10 enables that possibility, as will now be explained, for the preferred embodiment of FIG. 7.

In FIG. 7, sensor 82 receives and responds to all individualized entities transported by conduit 102. One must therefore examine the entity signals or waveforms themselves and determine whether the entity is a fiber, a nep, or a trash particle. It has been discovered that the improved sensor means, as disclosed in co-pending application Ser. No. 07/493,961, in combination with improved signal processing means (i.e. DAB 161 in FIG. 10) enables such classification and, thereby, meets the single sample/multiple data products objective. Whereas FIG. 10 describes in detail DAB operation for determination of length and diameter of individual fibers, FIG. 11 generalizes to show how signals from multiple entities are measured and, importantly, classified. To simplify FIG. 11, the low gain/high gain distinction is disregarded. This means that all signal voltages levels given below are referred to the high gain channel. The digital processing times (A/D conversions, resets, etc.) are also disregarded, so that all entities are examined. Accordingly, the arrival of an entity in the beam of sensor 82 will lead to analog signals shown in FIGS. 12a–12c and the corresponding digital signals TB, TE, TF, etc on line 212, 214, 222, etc. of FIG. 11.

Figure 12A:
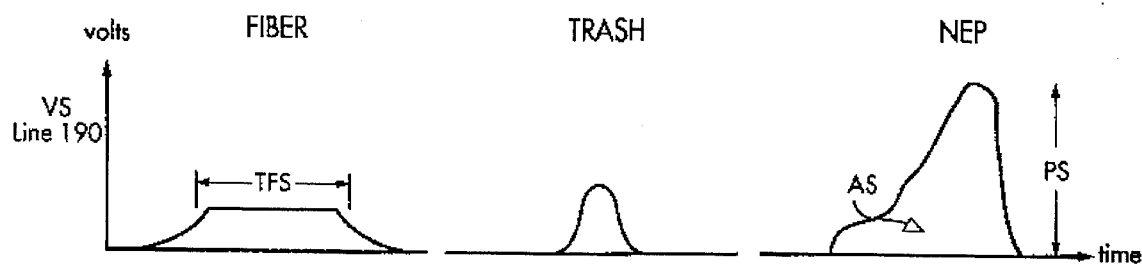
FIGS. 12a–12c shows analog waveforms from the sensor.
Figure 12B:
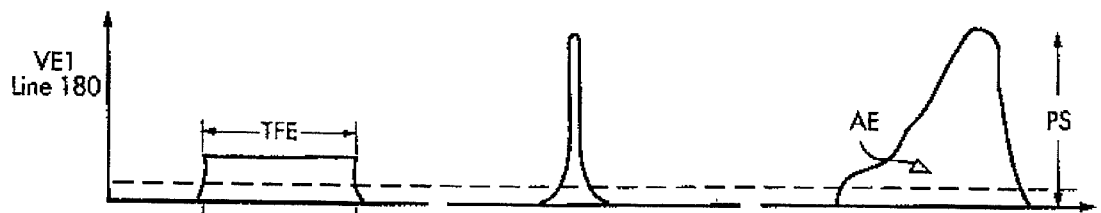
Figure 12C:
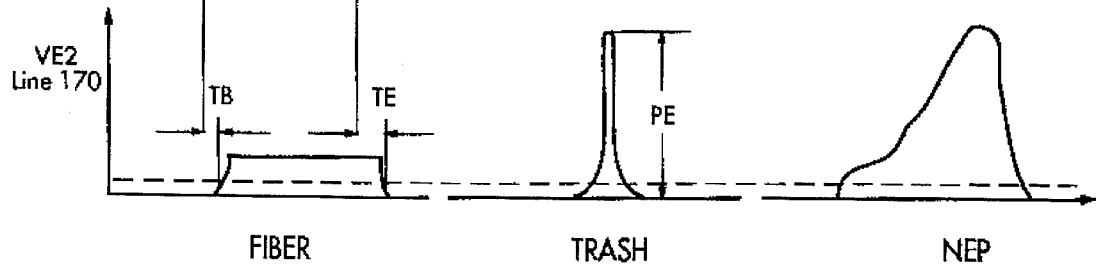
Figure 13:
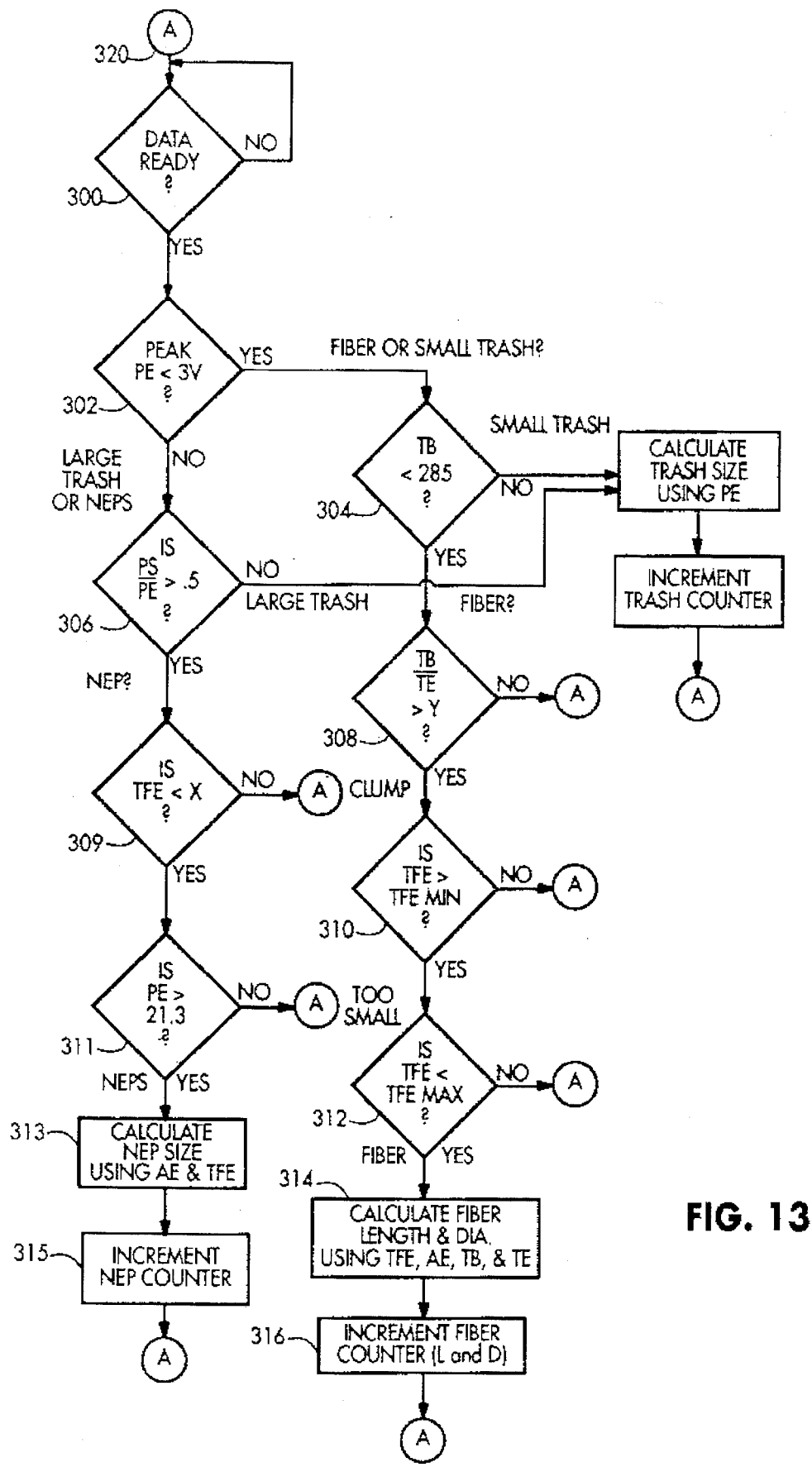
FIG. 13 is a flowchart illustrating how the computer acquires and analyzes data and classifies neps, trash and fiber data.

FIGS. 12a–12c illustrates typical analog signals or waveforms on the signal lines 170, 180 and 190 created by a fiber, a nep and a trash particle. The data acquisition board measures each of the three signals and passes to the computer, via the PC back plane, the eight parameters shown in FIGS. 12a–12c: TB, TE, TFE, TFS, PE, AE, AS and PS. These eight parameters are used to classify, count and size the three types of entities. This classification procedure is shown in flowchart form in FIG. 13, and the logical operation is as follows: The computer waits at block 300 for the DAB to signal that a pulse with peak amplitude greater than 0.5 V has been received. The first test at block 302 determines if the peak value on the extinction channel, PE, is less than 3 volts or greater. If PE is less than 3 volts the program moves to block 304 having eliminated the possibility that the pulse was a nep. If PE is greater than 3 volts the pulse is either a trash particle or a nep and the software moves to block 306.

If PE was less than 3 volts in block 302 and TB is less than 285 in block 304, (i.e. 285 counts of the 20 Mhz clock) a small trash pulse has been captured and the size of the trash particle is calculated from PE and the trash counter incremented. The size calibration is described in co-pending application Ser. No. 07/762,905.

If PE was less 3 volts in block 302 and TB is greater than 285 in block 304, the software has eliminated the possibility of a nep or trash particle and begins a set of tests to determine if the pulse is an acceptable fiber pulse in blocks 308, 310 and 312. If all 3 of the tests pass, the program calculates fiber length using TFE, TB and TE, calculates diameter using AE and TFE and increments the fiber counter in blocks 314 and 316. For staple textile fibers, we have discovered these preferable values: TB/TE>1.05 (value derived for each sensor during calibration); TFE min=100 and TFE max=10,000. (Values are counts of 10 MHz clock).

If PE was greater than 3 volts in block 302 and the ratio of PS to PE is less than 0.5 in block 306, a large trash pulse has been acquired. The size of the trash particle is calculated and the trash counter incremental as before.

If PE was greater than 3 volts in block 302 and the ratio of PS to PE is greater than 0.5, the software has eliminated the possibility of a fiber or a trash particle. The software tests the pulse in block 309 and block 311 to reject large clumps and small multiple fiber entanglements. A typical value for TFE<X is 300. If both tests and satisfied, a nep has been identified and its size is calculated from AE and TFE 313 and the nep counter 315 is incremented. Program control returns to the start block A 320 after each entity is identified.

Figure 14:
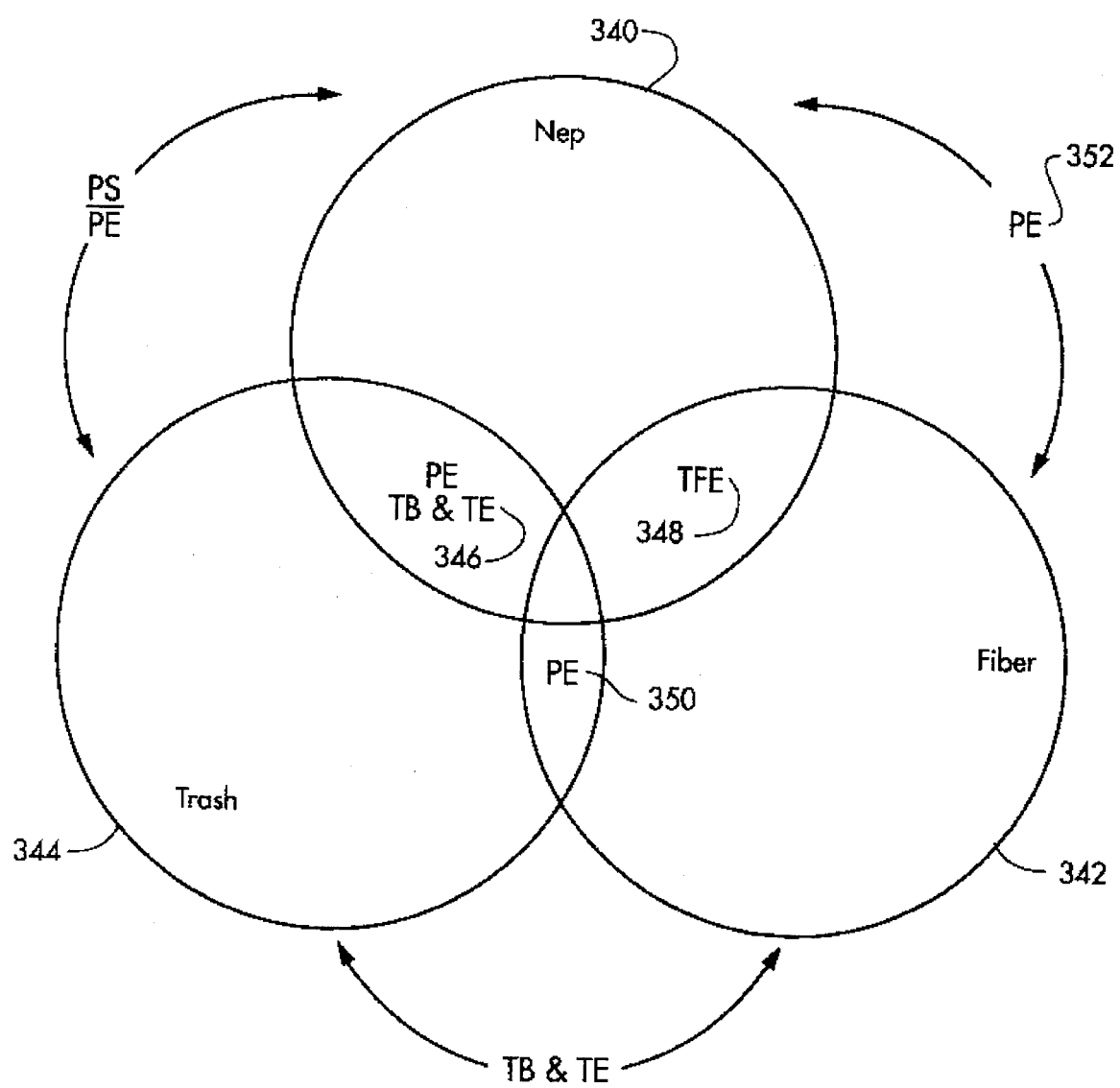
FIG. 14 is a Venn diagram showing the inter-relationship among the entity electro-optical parameters.

The relationship of the data from the DAB to the three entity types is shown in the Venn Diagram of FIG. 14. The three circles 340, 342 and 344 represent nep characteristics, trash particle characteristics and fiber characteristics. Characteristics that are common such as PE, TB and TE for nep 340 and trash 344 are inside the region of intersection 346. Characteristics that distinguish particles are shown outside the 3 circles 340, 342 and 344. An example would be parameter PE 352 for nep parameters 340 and fiber parameters 342. Using these parameter relationships, the flowchart, FIG. 13, was derived.

In the above described system, particles were broadly classified as fibers, neps or trash. Below, two variations of the system are described, one which sub-classifies trash and another which sub-classifies neps. These systems variations may be used separately or in combination depending upon the needs of a particular application.

Figure 15A:
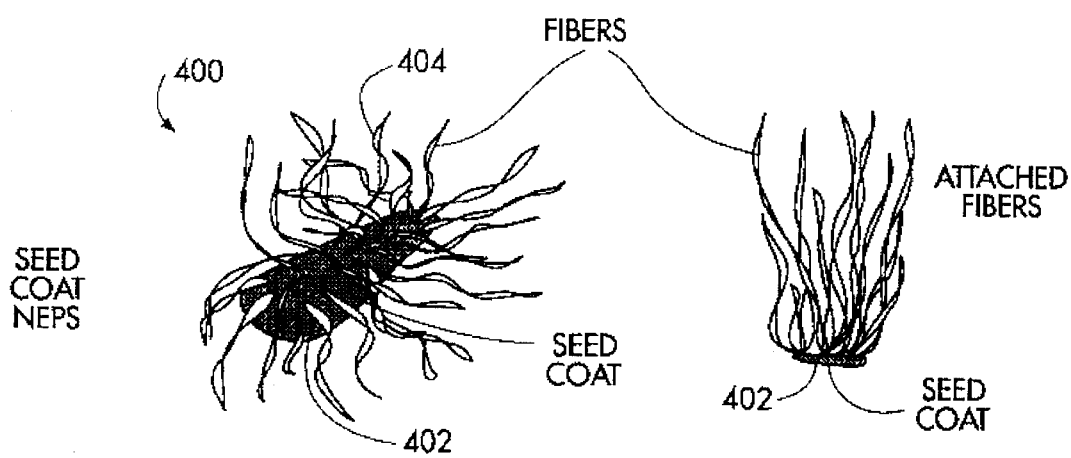
FIG. 15a, 15b and 15c are illustrations of three classes of neps.
Figure 15B:
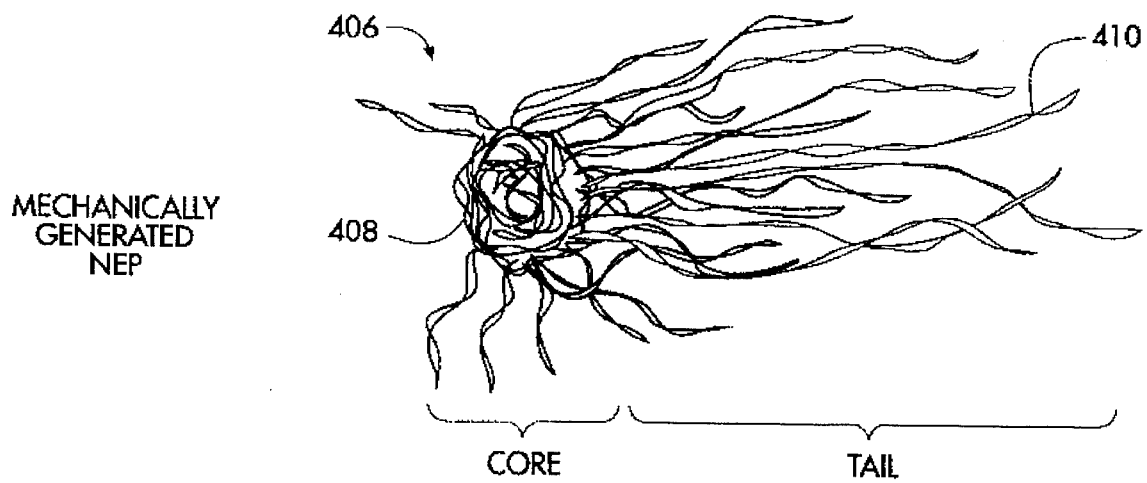
Figure 15C:
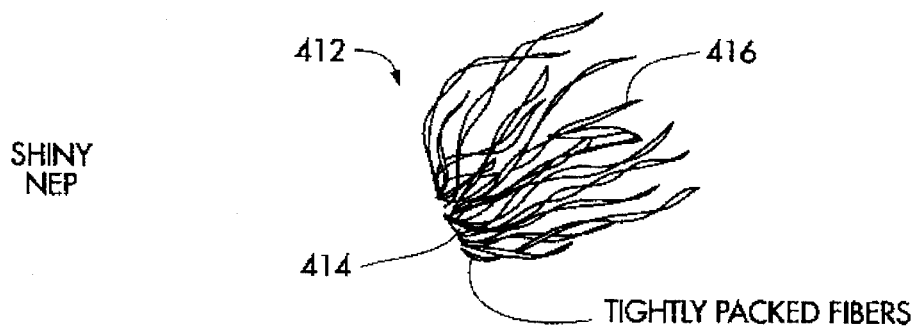

Before describing the neps sub-classification program, referring now to FIGS. 15a–15c, a better understanding of the nature of textile neps may be had. As was previously discussed, neps may generally be broken down into several categories, mechanically generated neps, shiny neps and seed coat fragments. As is shown in FIGS. 15a–15c, seed coat fragments 400 are generally made of a fragment of the cotton seed 402 to which cotton fibers 404 are attached. A mechanically generated nep 406 is generally comprised of a tangled core of fibers 408 along with a less dense tail of trailing fibers 410. Finally, a shiny nep 412 is generally made of a tightly tangled core 414 of immature fibers with a less dense tail of trailing fibers 416. Further, seed coat fragments may be subdivided into mature or immature fragments. Mechanically generated neps may also be subdivided into polyester neps, which fluoresce under ultraviolet light or others which do not.

Figure 16A:
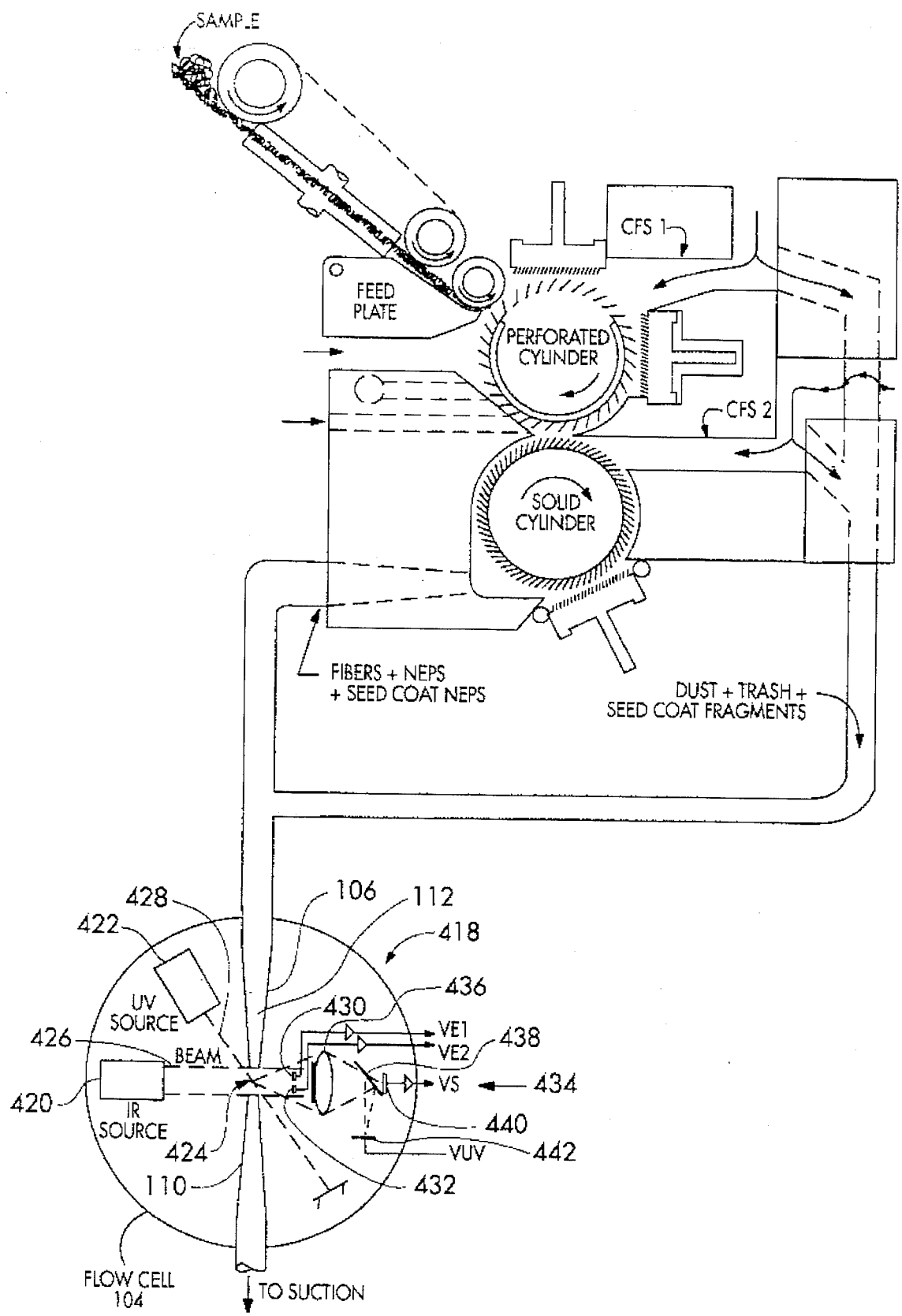
FIG. 16a shows an alternate sensor in the system of FIG. 7.
Figure 16B:
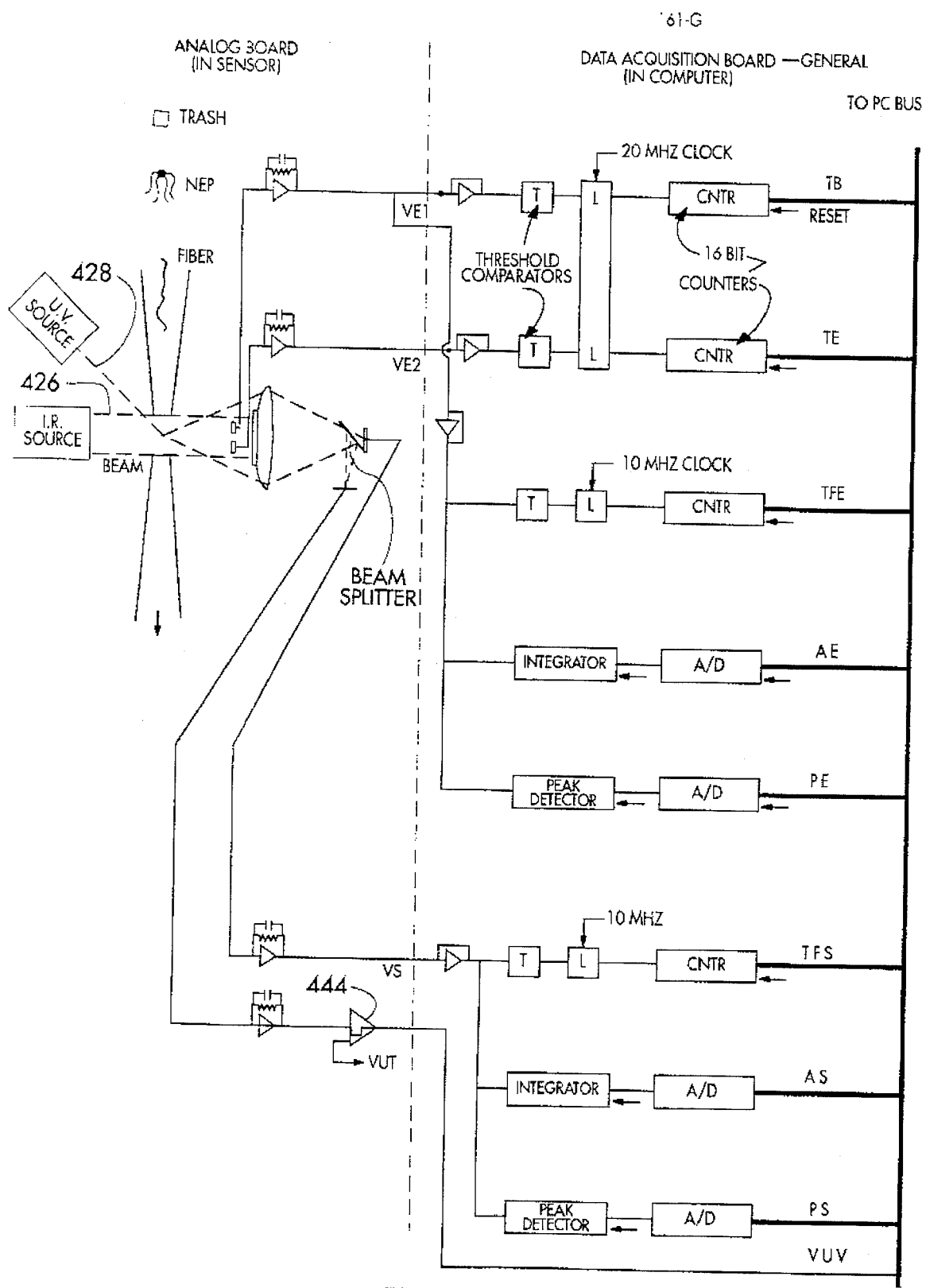
FIG. 16b shows the sensor of FIG. 16a as it is connected to the data acquisition board.

An alternate electro-optical sensor 418 and data acquisition electronics 161 are shown in FIG. 16a and 16b. The alternate embodiment provides for additional information of neps and trash in order to characterize them further. The alternate electro-optical sensor 418 consists of two radiation sources; an infrared source 420 having a wavelength of about 880 nm and an ultra-violet source 422 having a wavelength of about 370 nm. These sources propagate through the gap 424 between the two opposing nozzles 106 and 110 in the flow cell 104 to form an IR beam 426 and a UV beam 428. The IR source is received by a set of extinction detectors 430, 432 to measure the size and speed of the entity as it passes through the beam 426 as was previously discussed. A second detection system 434, located behind the imaging lens 436, collects the radiation scattered from the entity at angles from about 30 to 50 degrees. This system 434, is comprised of a beam splitter 438 and two detectors 440 and 442. The beam splitter 438 directs about one-half of the radiation to a fluorescence detector 442 which is sensitive to blue visible light (approximately 400 nm–480 nm). The remaining half of the radiation is directed to an IR detector 440 which is sensitive to the near infrared (approximately 880 nm). The detector 442 responds to the fluorescence (blue light) from the passage of polyester through the UV beam 428. All other common textile materials such as cotton and rayon do not exhibit UV fluorescence to a significant degree. The near infrared detector 440 responds to the 880 nm light scattered by the entity. This IR scattering provides information about the surface characteristics of the particle as was previously described with respect to the sensor of FIG. 11.

FIG. 16b shows the interconnection between the sensor 418 of FIG. 16a and the data acquisition board 161-G. The signals from the two extinction channels VE1 and VE2 are processed by the data acquisition board (DAB) 161-G (described previously with respect to FIGS. 10 and 11) to provide the speed of the particle. The speed of the particle is especially important in the classification of fiber neps as it is related to the mass of the entity. A particle with a larger mass, such as a seed coat nep, will not accelerate as rapidly in the flow stream 112 in the tapered section of nozzle 106 as a less massive particle and therefore will have a lower velocity while in the measurement volume.

Figure 11:
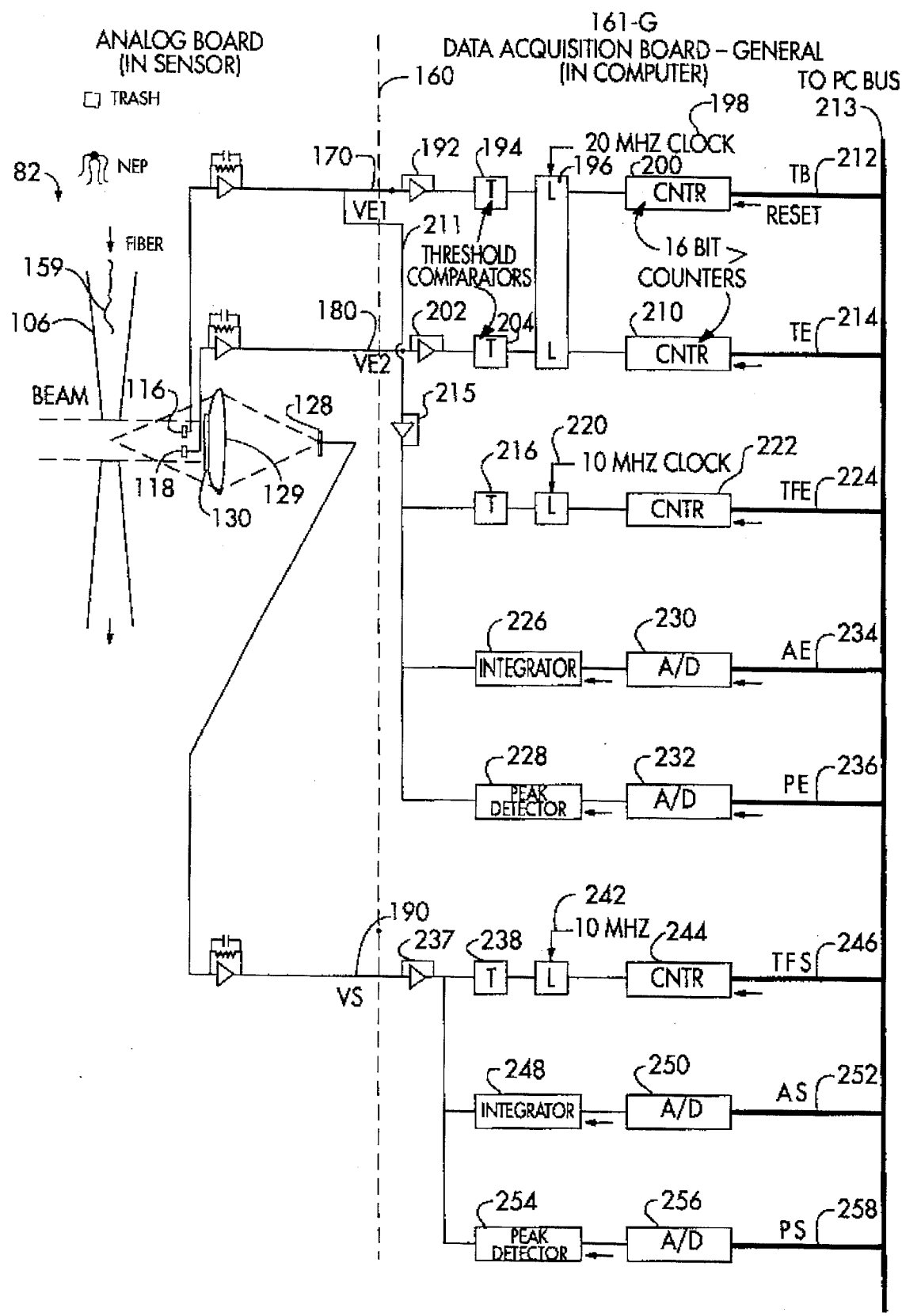
FIG. 11 is a generalized block diagram derived from FIG. 10.
Figure 17A:
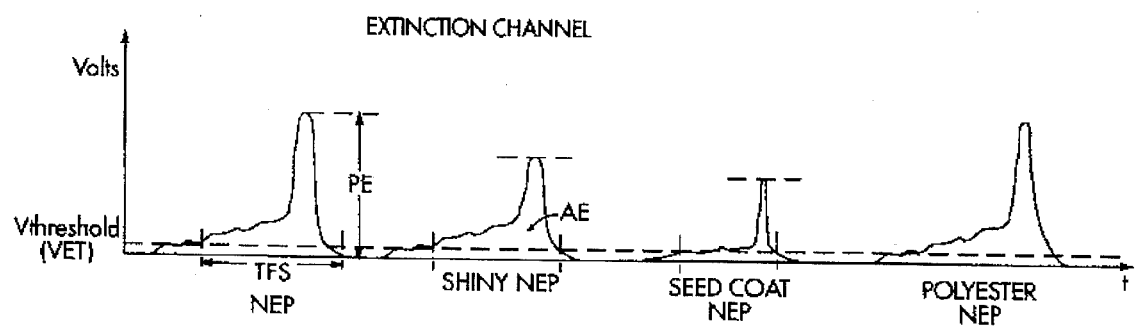
FIGS. 17a–17c are graphs of waveforms produced by various neps passing through the sensor of FIG. 16.
Figure 17B:
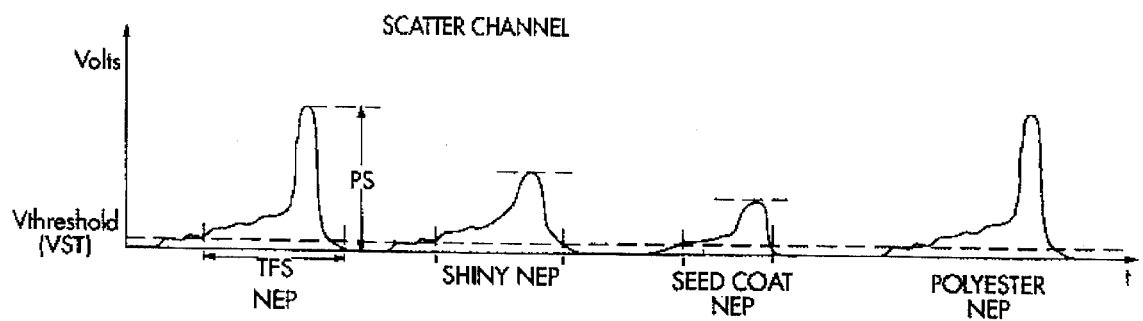
Figure 17C:
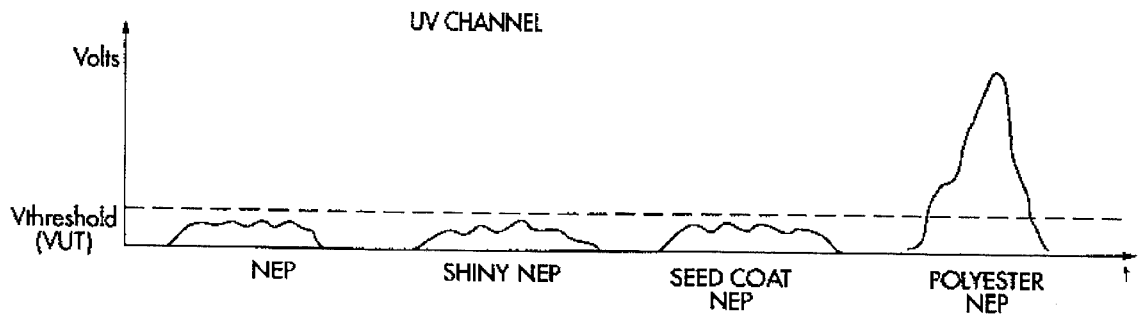

The first extinction channel signal VE1 is further processed as was previously described with respect to FIG. 11 to give the peak value of the signal (PE), the integrated value of the waveform above the threshold (AE) and the duration of the waveform above the threshold (TFE). Similarly, the scatter channel signal VS from the infrared scatter detector 440 is processed as previously described to yield PS, AS, and TFS. The signal from the fluorescence detector 442, VUV is coupled to a threshold comparator 444, whose threshold is set to respond to any significant amount of blue visible radiation above the electronic noise of the system, and the output of the comparator 444 is applied to the bus 213. The waveforms for a typical nep, shiny nep and seed coat nep are shown in FIGS. 17a–17c with the waveform parameters. With these waveforms in mind, the nep classification method described below may best be understood.

Figure 18A:
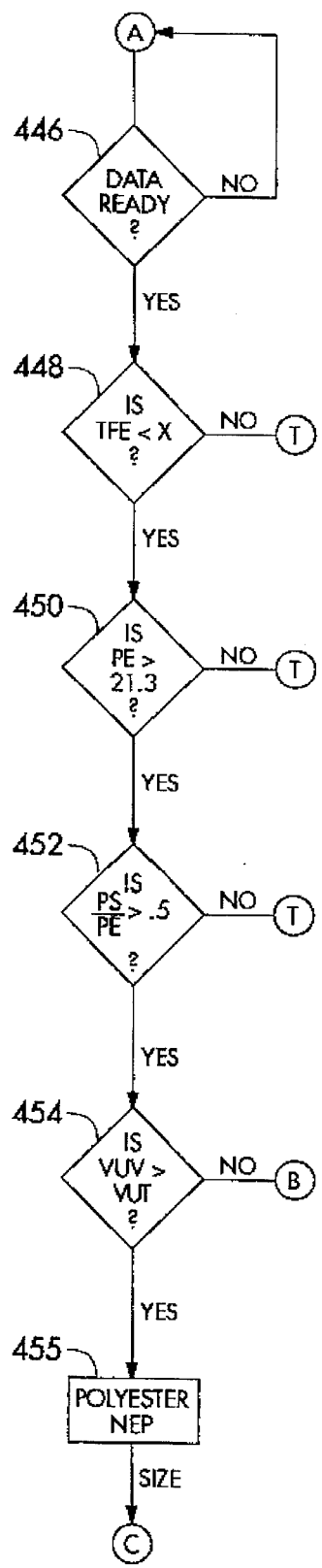
FIGS. 18a–18c are flow charts of a nep classification program.
Figure 18B:
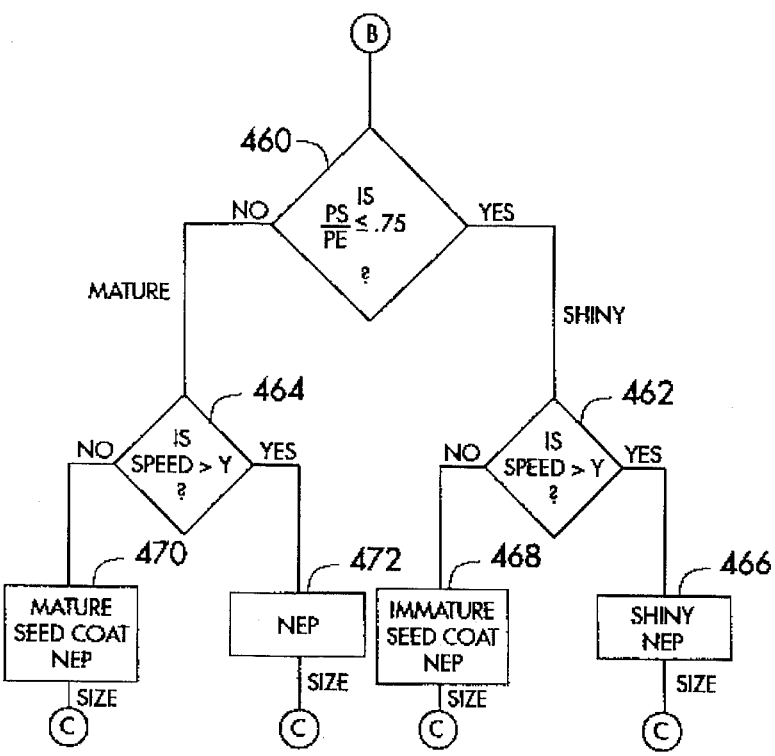
Figure 18C:
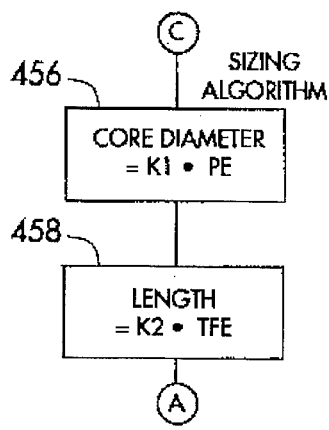
Figure 19:
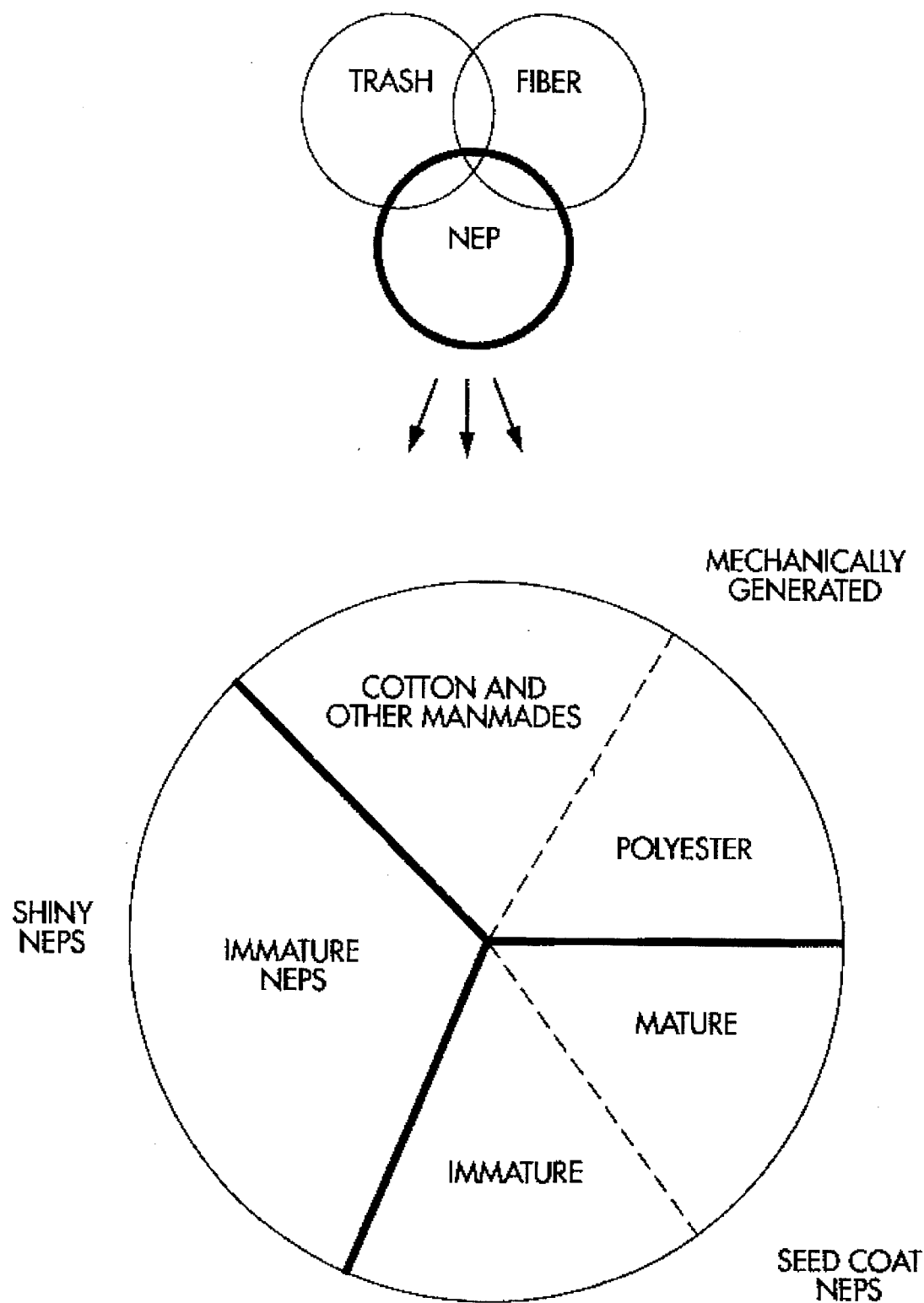
FIG. 19 is a pie chart showing the classes of neps.

Neps are classified according to the method illustrated in FIGS. 18a–18c in flow chart form. As illustrated in FIG. 19, the purpose of the classification method is to classify neps into groups, namely, mechanically generated neps, shiny neps and seed coat fragment neps. These classifications are further sub-classified as shown in FIG. 19 and discussed below.

The program (running on computer 18) waits at block 446 until a waveform appears on one of the channels. Then, it begins a series of three screening tests to determine if the event falls into one of the nep categories. If the event fails any of the three tests, control is passed to a trash classification program described hereafter. In the first test, the value of TFE must be small enough to exclude the possibility of counting a large clump of fibers, and the program checks whether TFE is less than X. The parameter X of block 448 is flow rate dependant and is normally chosen to exclude signals that are greater than approximately 30 μSec in duration when using current AFIS instruments. Second, the peak value of the signal must be greater than 21.3 V as shown in block 450. This defines the smallest group of fibers which will be defined as a nep. Third, the signal must contain enough information on the scatter channel, as determined by the ratio of PS/PE, to be processed as set forth in block 452. Any signal with a ratio less than 0.5 is not likely to be composed of fibers; i.e. such signals are usually due to trash particles and are ignored for the purposes of nep classification, but are further analyzed as possible trash particles.

At block 454, the UV channel (output of comparator 444) is checked to see if the event was a polyester nep as determined by the signal on the UV channel having a peak value greater than the threshold voltage (VUT). If yes, the size of the polyester nep is calculated as shown in blocks 456 and 458. If no signal is found on the UV channel, the program tests the ratio of PS to PE again as set forth in block 460 to determine whether or not the event was shiny (immature) or mature. If the ratio is less than or equal to 0.75, the event was due either to an immature seed coat nep or shiny nep and the speed test as set forth in block 462 determines which type of entity the event was. If the speed is greater than Y, the program classifies and reports the event as a shiny nep as indicated at block 466 and if speed is less than Y, the event is classified and reported as an immature seed coat nep as indicated at block 468.

The variable Y of blocks 462 and 464 is a flow rate dependant calibration parameter (expressed in meters per second (m/s)) that is optimized for particular system flow parameters. For a system operating at approximately 3.9 CFM, this value is typically 60 m/s. Once the particle is classified as either a seed coat nep or shiny nep it is sized as set forth in blocks 456 and 458. It is understood that separate sizing algorithms may be used for the different nep subclasses.

Also, the speed used in this program is preferably the average speed calculated by averaging TB and TE and dividing the effective distance between detectors 116 and 118 in FIG. 7 or detectors 430 and 432 in FIG. 16a by the average. Other speed calculations and measurements may also be used, such as a speed calculation based solely on TB, or solely on TE, or on an acceleration corrected time such as described in co-pending application entitled "Methods and Apparatus for Mechanically and Electronically Correcting Presentation of Entities in a Fluid Flow," filed Dec. 31, 1992, docket No. 48122.00. The value Y must be calibrated depending upon the flow rate of the system and the manner in which speed is calculated. Because of the speed differences between mechanical neps and mature seed coat neps, any of the speed calculations mentioned above may be used to distinguish between and classify these two types of neps.

If in block 460 the ratio of PS to PE is not less than or equal to 0.75, then the event was due to a mature entity and the event is tested as set forth in block 464 to determine if a mature seed coat nep was present. If speed is less than Y, it is determined that a mature seed coat nep is present, and the event is classified and reported as a mature seed coat nep as indicated at block 470 and then sized. If speed is greater than Y, there was no seed coat fragment, and the event is counted as a mature nep at block 472 and sized.

The sizing program as set forth in blocks 456 and 458 convert the peak value on the extinction channel, PE, to a physical size by the calibration constant K1 (microns/volt).

The length of the nep is preferably determined in this embodiment by multiplying TFE by the calibration parameter K2 which is the speed detected by the extinction detectors 430 and 432 as was also described previously.

Statistics such as the standard deviation of diameters, the number of counts per unit weight in each of the classes and a size frequency histogram may then be calculated by the computer 18 (FIG. 1) based upon the classifications.

It will be appreciated that neps may be further sub-classified using the system and methods discussed above. For example, sticky neps or "points" are found in cotton fibers and are typically caused by the sugars of insects that are harvested along with cotton. These sticky neps can cause gumming of the processing machinery and may be a concern. To detect sticky neps in the system described above, preferably, the infrared beam is chosen to have infrared frequency specific to a suspected sugar in the cotton and is chosen to avoid absorption by water. When a sticky nep is presented at the sensor 418, it will exhibit strong absorption of the infrared beam which will be detected by extinction detectors 430 and 432. Thus, once a nep is identified by the methods discussed above, it may be further sub-classified as a sticky nep or point by determining whether its absorption of sugar specific infrared light exceeds a predetermined threshold, which is determined by calibration for a particular system and will vary for different types of cottons from different geographical regions.

Figure 20:
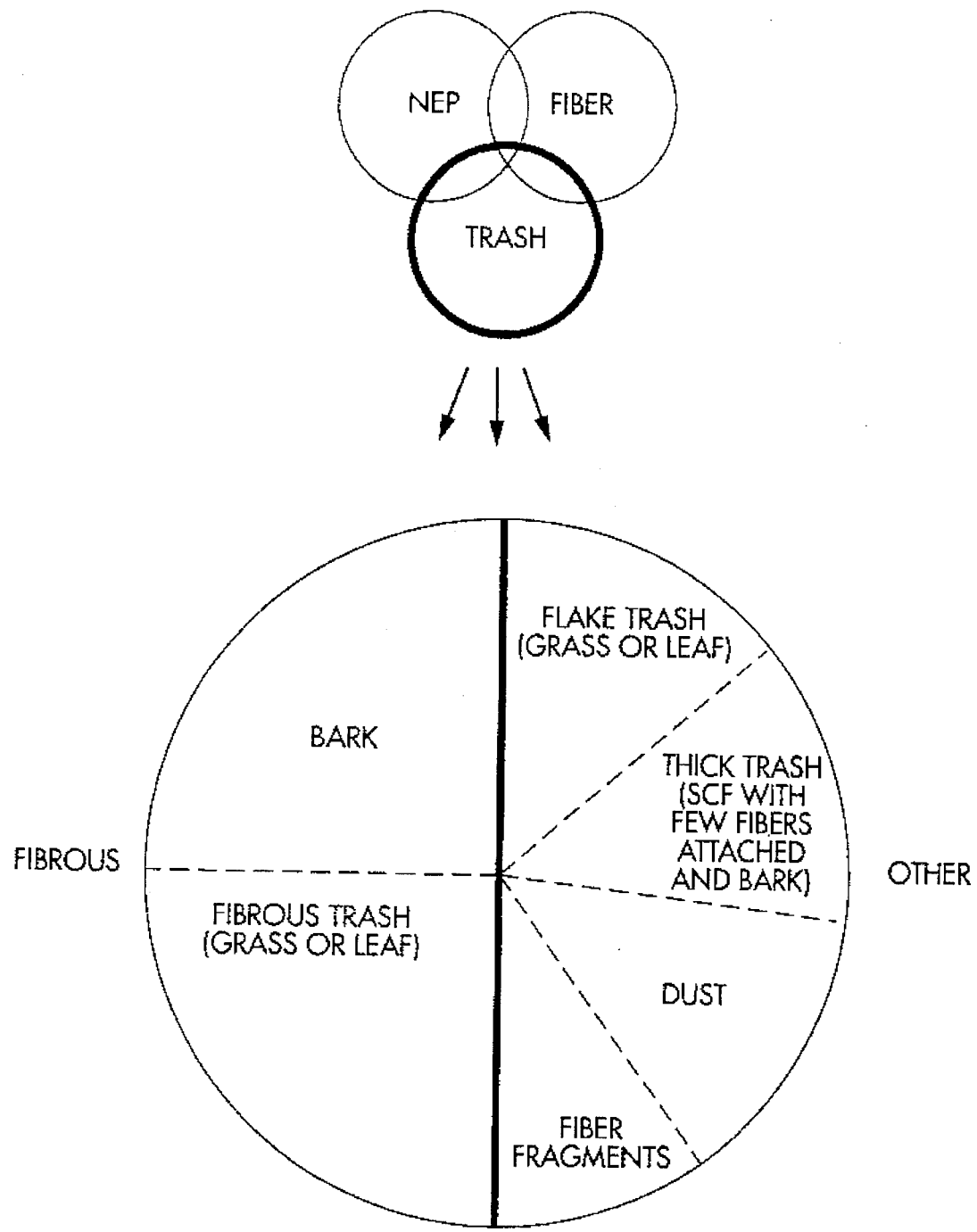
FIG. 20 is a pie chart showing the classes of trash.
Figure 21A:
FIGS. 21a–21e are is an illustration of various types of trash.
Figure 21A:
Figure 21B:
Figure 21B:
Figure 21C:
Figure 21C:
Figure 21D:
Figure 21D:
Figure 21E:
Figure 21E:

Having described the nep sub-classification system above, the trash sub-classification system will now be described. However, before describing this system, a better understanding of trash, particularly cotton trash, may be had be reference to FIGS. 20 and 21a-21c which show, respectively, a pie chart and illustrations of various types of trash. As shown in FIG. 20, trash may be divided into two broad classes or categories, fibrous and other. The category of "other" is not necessarily non-fibrous. For example, fiber fragments are classified as "other" because of their short length. Thus, it will be appreciated that the trash is being classified according to its physical characteristics. Generally, trash is considered to be fibrous if it has an aspect ratio or 3 or greater.

Referring to FIGS. 20 and 21a-21c, it will be appreciated that bark and leaf or grass having an aspect ratio of greater than 3 will be classified as fibrous. Flake trash having an aspect ratio of less than 3 is considered "other" trash and, likewise, thick trash, dust and fiber fragments having an aspect ratio of less 3 are considered to be "other" trash. Thick trash which is illustrated in FIG. 21 is typically a thick seed coat fragment with only a few fibers attached or a fragment of bark. In general, thick trash is any trash having a geometry approximating a sphere or a cube. The exact definition of thick trash will depend upon selected parameters in the classification program described below.

Figure 22A:
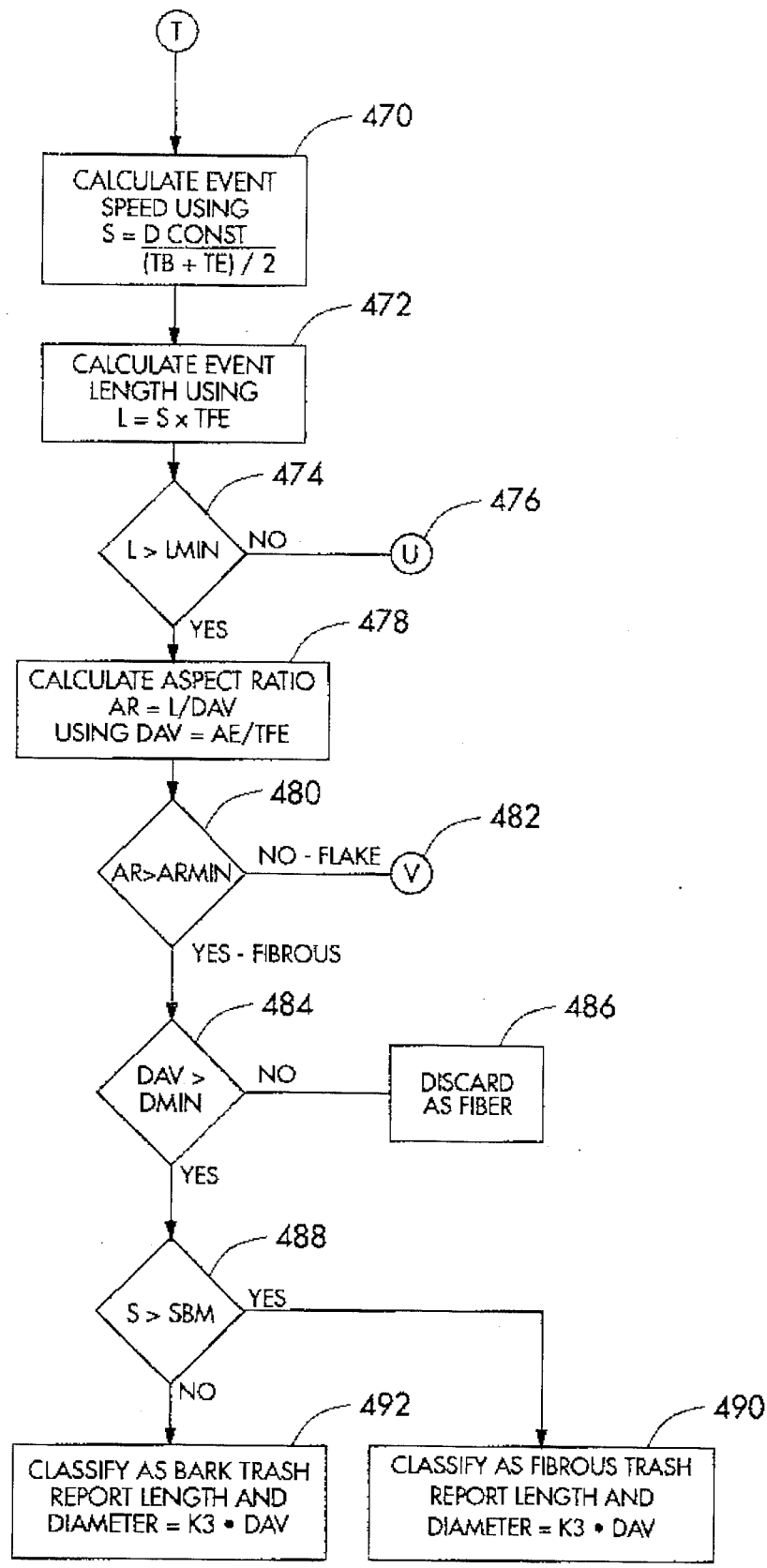
FIGS. 22a, 22b and 22c are flow charts of a trash classification program.

Referring now to FIG. 22a, there is shown a flow chart for classifying trash. This program begins at the circle labeled "T" and, referring to FIG. 18a-8c, it will be appreciated that the nep program is designed to transfer control to the trash program at three different positions in the program. Thus, the nep sub-classification program and the trash sub-classification program are designed to be able to run together, if desired. Of course, the trash program could run independently and this would be preferred where one knows that only trash will be detected by a particular or separate physical sensor system.

The first step in the trash sub-classification is indicated by block 470 wherein the speed of an event is calculated. In this particular embodiment speed (S) is preferably calculated by averaging TB and TE [(TB+TE)/2] and then dividing a constant (DCONST) by that average. Of course, DCONST is the effective distance between the extinction sensors 116 and 118 as shown in FIG. 7 or the extinction sensors 430 and 432 as shown in FIG. 16. Of course, if the beam, for example beam 426, impinging upon the detectors, for example detectors 430 and 432, is converging or diverging, DCONST is appropriately corrected to compensate for the magnification or reduction caused by the diverging or converging beams.

As indicated by block 472, the next step is to calculate the length of the event or entity using the formula L=S X TFE, where TFE is the time required for the entity to pass by one of the extinction sensors, L is length and S is speed. At decision step 474 the length is compared to a minimum length LMIN. If L is not greater than LMIN the program proceeds to point U indicated by character 476 and is transferred to another section of the program which will be described hereinafter. If L is greater than LMIN, the program proceeds to block 478 and calculates the aspect ratio (AR) which is the length (L) divided by the average diameter (DAV), where DAV is calculated using the formula DAV= AE/TFE. Proceeding to decision step 480, if the aspect ratio, AR is not greater than ARMIN, the event is regarded as a flake and the program passes to point "V" indicated by character 482. If AR is greater than ARMIN then the program continues to decision step 484. As previously discussed, by general industry agreement, an entity having an aspect ratio greater than 3 is considered fibrous. Thus, in the preferred embodiment, ARMIN is chosen to be 3. However, depending upon their application, it may be desirable to change the value of ARMIN in decision step 480. For example, in some applications, industry standards may define fibrous as an aspect ratio greater than 10.

At decision step 484, the program compares DAV to a minimum threshold (DMIN). If DAV is not greater than DMIN, the program moves to block 486 and discards the data regarding it to be data produced by a fiber. If DAV is greater than DMIN, the program moves to a decision step 488 and determines whether speed is greater than a chosen speed bark maximum (SBM). If S is greater than SBM, the program classifies the trash as fibrous trash and it reports the length of the trash and the diameter of the trash. Preferably, the diameter of the trash is reported as being equal to DAV times a constant K3. The constant K3 is a calibration constant that is determined experimentally. If S is not greater than SBM, the program classifies the trash as bark trash, reports the length and reports the diameter, again, as K3 multiplied by DAV, as indicated by block 492.

Figure 22B:
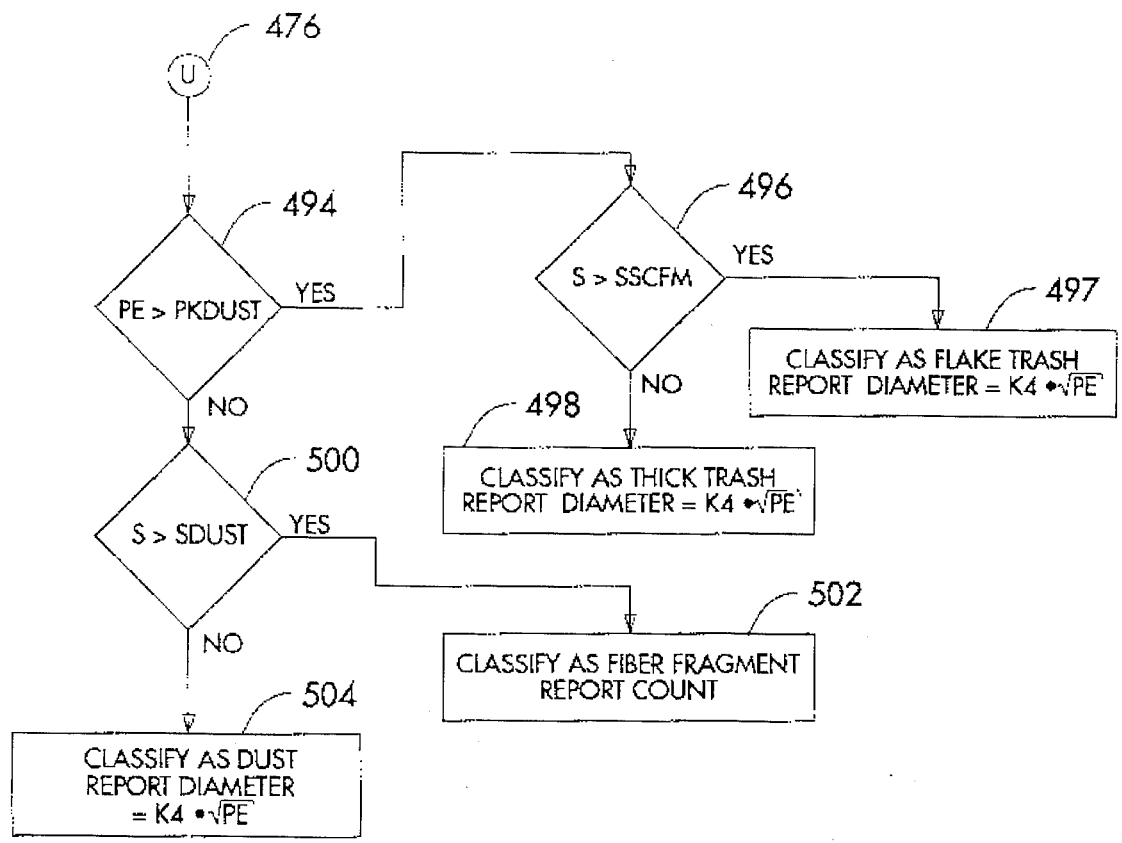
Figure 22C:
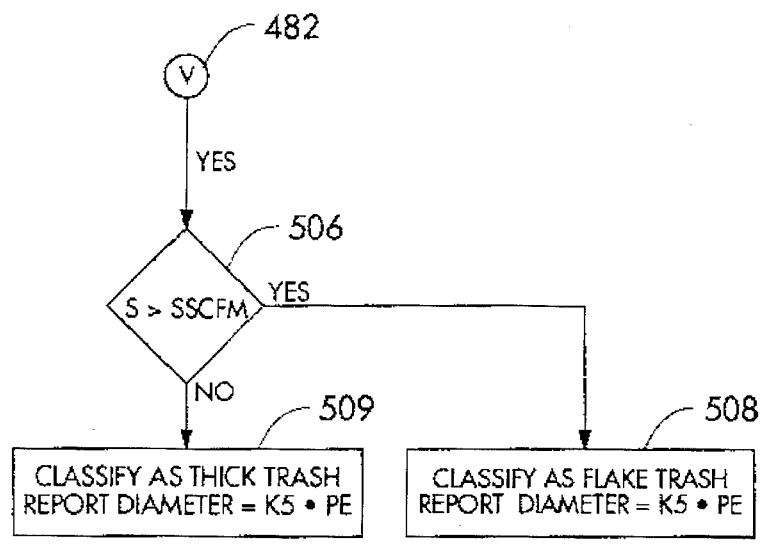

Returning to decision step 474, it will be recalled that if L was no greater than LMIN, the program transferred control to point U which is the sub-routine shown in FIG. 22b. Referring to FIG. 22b, the first decision step 494 compares the peak voltage (PE) to a threshold (PKDUST). If PE is greater than PKDUST, the program moves to decision step 496 where speed is compared to the constant (SSCFM) (Speed Seed Coat Fragment Max). If S is greater than SSCFM, as indicated at block 497, the program classifies the event as flake trash and reports the diameter of the trash as being equal to K4 multiplied by the square root of PE. If S is not greater than SSCFM, the program moves to block 498 and classifies the event as thick trash and reports the diameter as K4 multiplied by the square root of PE. K4 is a calibration constant and the constant PKDUST is chosen such that PE will be greater than PKDUST when a particle has a diameter greater than 500 microns.

Referring again to decision step 494, if PE is not greater than PKDUST, the program moves to decision step 500 and determines whether speed (S) is greater than a constant (SDUST). If yes, the program classifies the event as a fiber fragment and reports the count of fiber fragments as indicated by block 502. If no, the program classifies the event as dust and reports the diameter as K4 multiplied by the square root of PE, as indicated by block 504.

Referring to 22a and 22c, it will be recalled that if AR is not greater than a constant (ARMIN), the program moves to point 482 which begins another sub-routine, V. This sub-routine begins at step 506 where speed is compared to a constant (SSCFM). If yes, the program classifies the event as flake trash and reports the diameter as K5 multiplied by PE. If no, the program classifies the event as thick trash and reports the diameter, again, as K5 multiplied by PE.

Having described the operation of the trash classification program, some additional details are provided below that are specific to a particular application of the invention. These details should be regarded as examples and not limitations.

For example, the calibration parameters K1, K3–K5 are determined experimentally by placing known entities into the system. These parameters (K1, K3–K5) may be constants or curves. In the preferred embodiment, K4 is a curve which is stored within computer 18 in the form of a look-up table (PE), of selected peak extinction values (PE) and associated diameters. When a PE is sensed, the diameter is found by using the look-up table and interpolation where necessary.

Referring to decision step 474, the length of the event was tested against LMIN. Preferably LMIN is 1 mm, but other dimensions could be chosen. The philosophy for choosing this dimension is that, in this particular application, trash that has a length of less than 1 mm is "other" trash. It is not fibrous trash.

Referring to decision step 480, as previously mentioned, it is preferred to use ARMIN equal to 3. This decision step means that for trash to be classified as fibrous, it must have an aspect ratio of 3. Otherwise, it will be classified as "other." At step 484, the diameter of the trash is compared to DMIN. Preferably DMIN is 120 μm which corresponds to 12 volts in the AFIS circuitry described above. The underlying reason behind this test is to ensure that fiber has not somehow thus far been classified as trash. If DAV is not greater than 120 μm, the data are discarded as possibly being non-trash fiber data. Referring to decision step 488, the speed test is distinguishing between two types of fibrous trash. Grass and leaf trash, which is categorized as fibrous trash, will travel faster in an accelerating airstream than bark trash (which is also fibrous) because leaf and grass trash is less dense and usually has less mass. Consequently of course, bark is traveling at a slower speed than grass and leaf because of its mass and density.

Referring to decision step 494, this decision is based entirely on size. If an event is smaller than 500 microns which is the industry standard cutoff, the program classifies it as dust or a fiber fragment. At decision step 500, SDUST is preferably chosen to be 64 meters per second. This constant is highly dependent upon the flow rate of the gas or air in a particular system, since extremely small particles such as dust and fiber fragments will move at approximately the flow rate of the airstream.

Referring to decision steps 496 and 506, there is again a classification according to speed. In this particular application, SSCFM is chosen to be 30 meters per second and it functions to distinguish between flake trash and thick trash. In this case, flake trash has a greater surface area per unit weight than thick trash and, thus, will travel faster in an accelerating airstream. The actual value for SSCFM should be determined by calibration by injecting known flake trash and known thick trash and observing their speeds. As previously mentioned, these specific numbers should be regarded as examples and it will be understood that they will vary depending upon air flow rates, nozzle configuration, sensor system, amplification systems, etc.

It should be noted that the values given above are for use in the system described with reference to FIGS. 10, 11 and 16a. If different gain values are used or different components are substituted, these values would naturally have to be changed to correspond to the modified system. One way to determine these values for a new system would be to drop a series of known entities through the sensor section and measure the values of the characteristic parameters. Then, these values could be provided to the computer for use in the classification program to be used with unknown test samples. It should be further noted that the sensor of FIG. 16a is similar to that of FIG. 11 and adds the UV light source 422, beam splitter 438, fluorescence detector 442 and its associated electronics. The remaining components function substantially as was described previously.

While several embodiments of the invention have been described in the foregoing Detailed Description, it will be understood that the invention is capable of numerous rearrangements, modifications and substitutions of parts without departing from the scope of the invention as defined by the appended claims.

What is claimed is:

1. An apparatus for measuring characteristics of entities in a sample of textile material, including different types of trash, said types of trash selected from the group consisting of: bark, fiber fragment, dust, thick trash and flake trash, the apparatus comprising:

supply means for supplying a sample of textile material;

a processor including a processor input and a processor output, said processor input being positioned and operable to receive the textile sample from said supply means, said processor being operable for processing said sample, releasing the entities of said sample one from the others, individualizing the entities of the sample to produce single entities, and producing entities at said processor output in an individualized condition;

sensor means;

a transport for transporting individualized ones of said entities to said senor means;

said sensor means being operable to sense at least one characteristic of a portion of the entities, including trash, being moved by said transport and for producing characteristic signals corresponding to said sensed characteristics; and analysis means for receiving said characteristic signals, analyzing said characteristic signals to identify signals that correspond to at least trash, said analysis means comprising:
means for determining the speed of an entity sensed by said sensor means based on the characteristic signals;
means for determining the length of an entity based on the characteristic signals;
means for comparing the length of an entity to a length threshold;
means for determining a diameter that corresponds to a diameter characteristic of the entity sensed by the sensor based upon the characteristic signals, if the length is greater than the length threshold;

means for determining an aspect ratio based upon the length compared to the diameter and for comparing the ratio to an aspect ratio threshold, if the length is greater than the length threshold;

means for comparing the diameter to a diameter threshold, if the length is greater than the length threshold and the aspect ratio is greater than the aspect ratio threshold;

means for comparing the speed to a bark speed max, if the length is greater than the length threshold and the aspect ratio is greater than the aspect ratio threshold and the diameter is greater than the diameter threshold;

means for classifying the entity as bark trash, if the speed is not greater than the bark speed max, and as fibrous trash, if the speed is greater than the bark speed max;

means for determining a peak value based upon said characteristic signals for a trash entity;

means for comparing said peak value to a peak threshold, if the length is less than the length threshold;

first means for comparing the speed to a seed coat fragment max, if the peak value is greater than the peak threshold;

means for classifying the entity as flake trash, if the speed is greater than the seed coat fragment max and the peak value is greater than the peak threshold, and for classifying the entity as thick trash, if the speed is not greater than the seed coat fragment max and the peak value is greater than the peak threshold;

means for comparing the speed to a dust max;

means for classifying the entity as a fiber fragment if the speed is greater than the dust max, and for classifying the entity as dust, if the speed is not greater than the dust max;

second means for comparing the speed to a seed coat fragment max, if the aspect ratio is not greater than the aspect ratio threshold; and means for classifying the entity as thick trash, if the speed is not greater than the seed coat fragment max and the aspect ratio is not greater than the aspect ratio threshold, and for classifying the entity as flake trash, if the speed is greater than the seed coat fragment max and the aspect ratio is not greater than the aspect ratio threshold.

\* \* \* \* \*